United States Patent
Kubo

(10) Patent No.: US 10,893,810 B2
(45) Date of Patent: Jan. 19, 2021

(54) IMAGE PROCESSING APPARATUS THAT IDENTIFIABLY DISPLAYS BLEEDING POINT REGION

(71) Applicant: OLYMPUS CORPORATION, Tokyo (JP)

(72) Inventor: Kei Kubo, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 121 days.

(21) Appl. No.: 16/263,385

(22) Filed: Jan. 31, 2019

(65) Prior Publication Data

US 2019/0159687 A1    May 30, 2019

Related U.S. Application Data

(63) Continuation of application No. PCT/JP2017/033046, filed on Sep. 13, 2017.

(30) Foreign Application Priority Data

Nov. 1, 2016  (JP) .................................. 2016-214564

(51) Int. Cl.
*A61B 5/02* (2006.01)
*G06T 7/00* (2017.01)
(Continued)

(52) U.S. Cl.
CPC ...... *A61B 5/02042* (2013.01); *A61B 1/00009* (2013.01); *A61B 1/00105* (2013.01);
(Continued)

(58) Field of Classification Search
CPC ............ A61B 5/02042; A61B 1/00105; A61B 5/1459; A61B 1/0646; A61B 1/0684;
(Continued)

(56) References Cited

U.S. PATENT DOCUMENTS

2008/0294105 A1    11/2008  Gono et al.
2009/0303319 A1    12/2009  Sato et al.
(Continued)

FOREIGN PATENT DOCUMENTS

JP    2002-095635 A    4/2002
WO    2008/102803 A1    8/2008
(Continued)

OTHER PUBLICATIONS

McGill, Schools Wikipedia Selection: General Physics "Colour"; 2007; URL: https://www.cs.mcgill.ca/~rwest/wikispeedia/wpcd/wp/c/Color.htm (Year: 2007).*

(Continued)

*Primary Examiner* — Siamak Harandi
(74) *Attorney, Agent, or Firm* — Scully, Scott, Murphy & Presser, P.C.

(57) ABSTRACT

A video processor includes: a region extracting circuit that receives an input of a first image signal obtained by forming an image of a subject irradiated with first narrow band light including a wavelength that is minimally absorbed by blood within a green wavelength band, the image of the subject including a bleeding point, and extract a blood pool region having a blood concentration that is lower than a blood concentration of the bleeding point in a region representing the blood in the first image signal; and an image generating circuit that raises a luminance value of the blood pool region in either the first image signal or a second image signal obtained by forming an image of the subject irradiated with second narrow band light whose wavelength is shorter and which is more absorbed by the blood than the first narrow band light.

7 Claims, 15 Drawing Sheets

(51) Int. Cl.
*G06T 7/11* (2017.01)
*H04N 5/225* (2006.01)
*A61B 5/1459* (2006.01)
*A61B 1/06* (2006.01)
*A61B 1/045* (2006.01)
*A61B 1/05* (2006.01)
*A61B 1/00* (2006.01)
*A61B 5/00* (2006.01)
*G02B 23/24* (2006.01)
*A61B 1/04* (2006.01)
*A61B 1/055* (2006.01)

(52) U.S. Cl.
CPC .............. *A61B 1/042* (2013.01); *A61B 1/045* (2013.01); *A61B 1/05* (2013.01); *A61B 1/0638* (2013.01); *A61B 1/0646* (2013.01); *A61B 1/0684* (2013.01); *A61B 5/0084* (2013.01); *A61B 5/1459* (2013.01); *G02B 23/2484* (2013.01); *G06T 7/0012* (2013.01); *G06T 7/11* (2017.01); *H04N 5/2256* (2013.01); *A61B 1/055* (2013.01); *G06T 2207/10024* (2013.01); *G06T 2207/10068* (2013.01); *G06T 2207/10152* (2013.01); *G06T 2207/30104* (2013.01); *H04N 2005/2255* (2013.01)

(58) Field of Classification Search
CPC ....... A61B 1/045; A61B 1/05; A61B 1/00009; A61B 1/0638; G02B 23/2484; H04N 5/2256; G06T 7/0012; G06T 7/11
See application file for complete search history.

(56) References Cited

U.S. PATENT DOCUMENTS

2014/0213871 A1   7/2014   Watanabe
2016/0262597 A1*   9/2016   Danchinyu ......... A61F 9/00821

FOREIGN PATENT DOCUMENTS

WO   2008/102803   *   2/2009   ............... A61B 1/00
WO   2013/051431 A1   4/2013
WO   2013/145407 A1   10/2013

OTHER PUBLICATIONS

International Search Report dated Nov. 21, 2017 received in PCT/JP2017/033046.

* cited by examiner

IMAGE PROCESSING APPARATUS THAT IDENTIFIABLY DISPLAYS BLEEDING POINT REGION

CROSS REFERENCE TO RELATED APPLICATION

This application is a continuation application of PCT/JP2017/033046 filed on Sep. 13, 2017 and claims benefit of Japanese Application No. 2016-214564 filed in Japan on Nov. 1, 2016, the entire contents of which are incorporated herein by this reference.

BACKGROUND OF THE INVENTION

1. Field of the Invention

The present invention relates to an image processing apparatus and specifically relates to an image processing apparatus that, when a mucous surface is covered by blood, can clearly display a site causing the bleeding, that is, a bleeding point.

2. Description of the Related Art

Conventionally, in a medical field, various minimally invasive tests and surgical operations using an endoscope have been performed. A surgeon inserts an endoscope into a body cavity and observes an image of a subject picked up by an image pickup apparatus provided in a distal end portion of an insertion portion of the endoscope and as necessary, can perform treatment of a lesion area using a treatment instrument inserted through a treatment instrument channel. Surgical operations using an endoscope do not need to open the abdomen or the like and thus have the advantage of imposing less stress on the body of a patient.

Endoscope apparatuses each include an endoscope, an image processing apparatus connected to the endoscope, and an observation monitor. An image of a lesion area is picked up by an image pickup device provided in a distal end portion of an insertion portion of the endoscope, the picked-up image is subjected to image processing by the image processing apparatus, and the image subjected to the image processing is displayed on the monitor. A surgeon can perform diagnosis or necessary treatment while viewing the image displayed on the monitor.

Also, some endoscope apparatuses can allow not only normal light observation using white light, but also special light observation using special light such as infrared light in order to observe blood vessels inside.

In the case of an infrared endoscope apparatus, for example, indocyanine green (ICG) having a characteristic of having an absorption peak for infrared light of around a wavelength of 805 nm is injected to the blood of a patient as a medical agent. Then, infrared light of around a wavelength of 805 nm and infrared light of around a wavelength of 930 nm are applied to a subject in a time division manner from a light source apparatus. A signal of an image of the subject picked up by a CCD is inputted to a processor in the infrared endoscope apparatus. For such infrared endoscope apparatus, an apparatus including a processor configured to allocate an image of around a wavelength of 805 nm to a green signal (G) and an image of around a wavelength of 930 nm to a blue signal (B) and output the green signal (G) and the blue signal (B) to a monitor has been proposed. Since an image of infrared light of around 805 nm, which is largely absorbed by ICG, is allocated to green, a surgeon can observe a resulting infrared image when ICG is administered, with good contrast.

For example, in an endoscopic submucosal dissection (hereinafter referred to as "ESD") for dissecting and resecting a submucosal layer in which a lesion area is present using an endoscope, a surgeon performs treatment such as dissection while identifying a position of a relatively thick blood vessel in a mucous membrane in order to avoid cutting such blood vessel via, e.g., an electronic surgical knife. Blood vessels that are likely to cause severe bleeding run from the submucosal layer to the proper muscular layer. Each time severe bleeding occurs in a procedure such as ESD, it is necessary to perform work for stopping the bleeding, resulting in lengthening of the procedure.

However, in order to identify a position of a blood vessel using the aforementioned infrared endoscope apparatus, as described above, complicated work of intravenously injecting a medical agent such as ICG is needed.

Also, the above-stated infrared endoscope apparatus has a problem of blood vessels in an image being blurred because wavelengths of illuminating light are wavelengths of near-infrared light.

Therefore, as in the disclosure of International Publication No. 2013/145407, endoscope apparatuses capable of clearly displaying a blood vessel in a deep part of a mucous membrane without complicated work of administering a medical agent, by generating an image signal of a wavelength band having a spectral peak wavelength in a range of from 585 nm to 615 nm and displaying an image based on the image signal have been proposed.

An endoscope apparatus according to such proposal can provide display on a monitor in such a manner that a site causing bleeding, that is, a bleeding point can be viewed when a mucous surface is covered by blood.

SUMMARY OF THE INVENTION

An image processing apparatus according to an aspect of the present invention includes: a region extracting circuit configured to receive an input of a first image signal obtained as a result of forming an image of a subject irradiated with first narrow band light including a wavelength within a range of from 505 nm to 515 nm as a center wavelength in a green wavelength band, the wavelength being minimally absorbed by blood, and extracts, of a bleeding point and a blood pool region having a blood concentration that is lower than a blood concentration of the bleeding point in the image of the subject, the blood pool region from the first image signal; and an image generating circuit configured to subject the blood pool region extracted by the region extracting circuit in the image of the subject generated using the first image signal to processing for displaying the blood pool region in a color that is different from a color of the bleeding point.

An image processing apparatus according to an aspect of the present invention is a processor including hardware, wherein: the processor receives an input of a first image signal obtained as a result of forming an image of a subject irradiated with first narrow band light including a wavelength within a range of from 505 nm to 515 nm as a center wavelength in a green wavelength band, the wavelength being minimally absorbed by blood, and extracts, of a bleeding point and a blood pool region having a blood concentration that is lower than a blood concentration of the bleeding point in the image of the subject, the blood pool region from the first image signal; and the processor subjects the extracted blood pool region in the image of the subject generated using the first image signal to processing for displaying the blood pool region in a color that is different from a color of the bleeding point.

DETAILED DESCRIPTION OF THE PREFERRED EMBODIMENT(S)

Embodiments of the present invention will be described below with reference to the drawings.

First Embodiment

Figure 1:
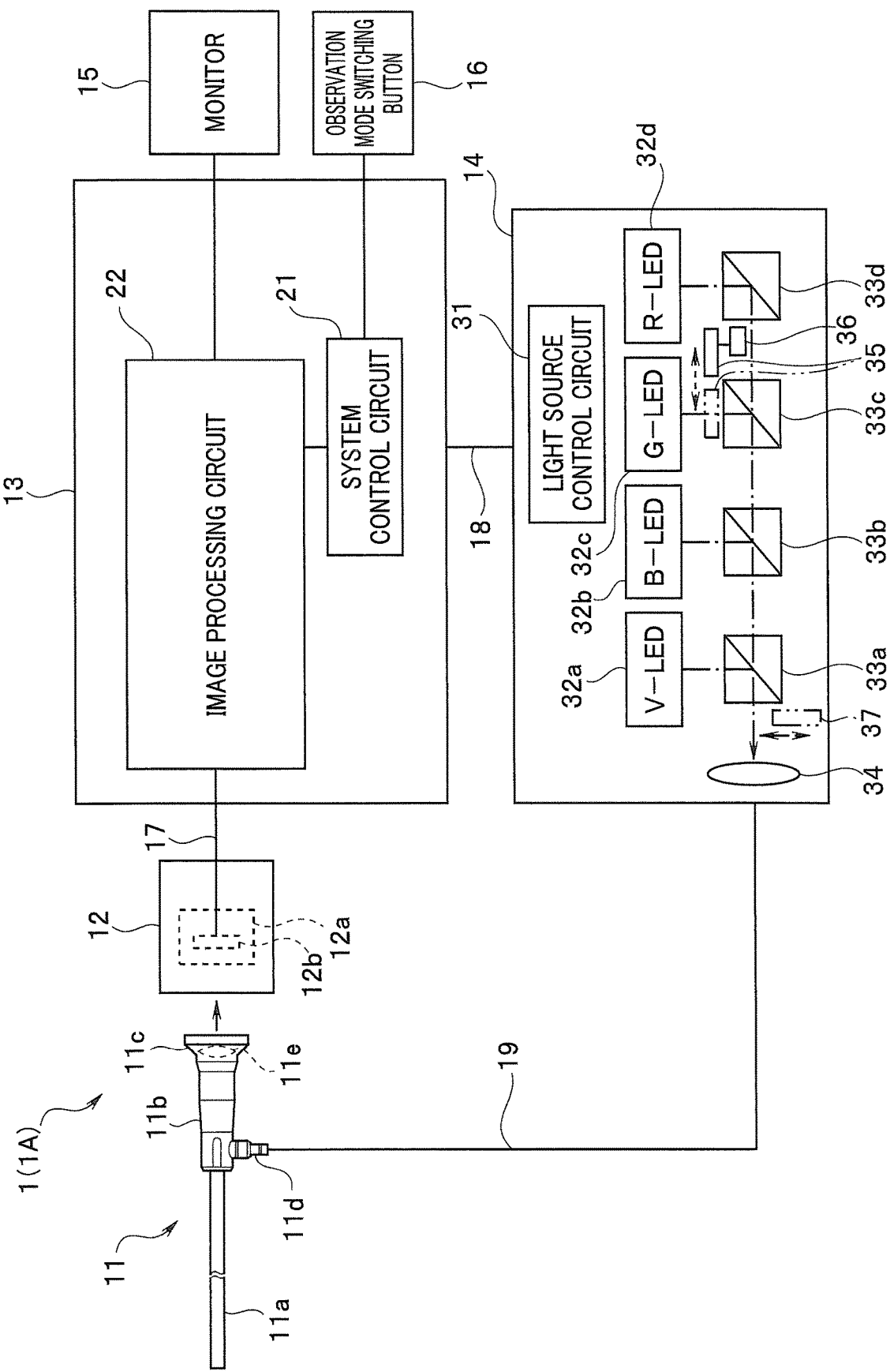
FIG. 1 is a configuration diagram illustrating a configuration of an endoscope apparatus including an image processing apparatus according to a first embodiment of the present invention.

FIG. 1 is a configuration diagram illustrating a configuration of an endoscope apparatus including an image processing apparatus according to the present embodiment.

An endoscope apparatus 1 includes a rigid endoscope 11, a camera head 12, a video processor 13, a light source apparatus 14, a monitor 15 and an observation mode switching button 16. The camera head 12 is connected to the video processor 13 via a cable 17. The video processor 13 is connected to the light source apparatus 14 via a cable 18.

The rigid endoscope 11 is a rigid endoscope including an elongated insertion portion 11a, a grasping portion 11b provided at a proximal end of the insertion portion 11a and an eyepiece portion 11c provided at a proximal end portion of the grasping portion 11b. A light guide connector 11d is provided at the grasping portion 11b. A lens 11e is incorporated in the eyepiece portion 11c. An end of a light guide cable 19 extending from the light source apparatus 14 is connectable to the light guide connector 11d.

An observation window (not illustrated) and an illumination window (not illustrated) are provided at a distal end portion of the insertion portion 11a. Light entering from the observation window is outputted from the lens 11e through an optical system, such as a rod lens, provided inside the insertion portion 11a. Illuminating light from the light source apparatus 14 enters the light guide connector 11d through a light guide inside the light guide cable 19. The illuminating light that has entered the light guide connector 11d is outputted from the illumination window through an optical system, such as a light guide, provided inside the insertion portion 11a.

As indicated by an arrow, the eyepiece portion 11c of the rigid endoscope 11 is attachable to the camera head 12.

The camera head 12 incorporates a lens system (not illustrated) and an image pickup section 12a. The image pickup section 12a includes an image pickup device 12b that has a light receiving surface that receives light passed through the lens system and is configured to perform photoelectric conversion of an image of the received light.

Here, the image pickup device 12b is a CMOS image sensor including an on-chip color filter. The color filter is a filter of RGB, which are three primary colors of light.

Here, the rigid endoscope 11 is separate from the camera head 12 including the image pickup device 12b, but the rigid endoscope 11 may be integral with the camera head 12. Therefore, the rigid endoscope 11 and the camera head 12 configure an endoscope including an image pickup device.

The image pickup section 12a outputs an image pickup signal to the video processor 13 via a signal wire inside the cable 17.

The video processor 13 is an image processing apparatus including a system control circuit 21 and an image processing circuit 22.

The system control circuit 21 includes a central processing unit (hereinafter referred to as "CPU"), a ROM and a RAM, and performs control of the image pickup section 12a of the camera head 12, the image processing circuit 22 and the light source apparatus 14. Software programs for providing various functions of the endoscope apparatus 1 are stored in the ROM.

The video processor 13 includes a non-illustrated operation panel, and a user, that is, a surgeon, a nurse or the like can set or change an operation mode of the endoscope apparatus 1 or provide various instructions and perform various adjustments by operating the operation panel and the observation mode switching button 16.

Therefore, the system control circuit 21 performs control of overall operation of the endoscope apparatus 1 by the CPU reading a program according to an instruction provided by the user from the ROM and executing the program, and performs control of the image pickup section 12a and the light source apparatus 14 according to an instruction provided by the user.

The image processing circuit 22 receives an image pickup signal from the image pickup section 12a and performs various types of image processing on the image pickup signal.

The endoscope apparatus 1 has three observation modes, here, a normal light observation mode, a narrow band light observation mode and a bleeding point observation mode.

The normal light observation mode is a mode in which when a subject is irradiated with white light, images of the subject obtained from reflected light from the subject is generated and image signals of the image are outputted to the monitor 15.

The narrow band light observation mode is a mode in which a subject is irradiated with one or two or more predetermined types of narrow band light (here, two types of narrow band light), images of the subject obtained from reflected light from the subject is generated and image signals of the images are outputted to the monitor 15. The narrow band light observation mode is used when, e.g., capillary blood vessels in the superficial portion of a mucous membrane are observed.

The bleeding point observation mode is a mode in which in order to display a bleeding point of a subject, the subject is irradiated with one or two or more predetermined types of narrow band light (here, three types of narrow band light), an image of the subject obtained from reflected light from the subject is generated and image signals of the image are outputted to the monitor 15. The bleeding point observation mode is used for identifying a site causing bleeding, that is, a bleeding point when a mucous surface is covered by blood.

The observation mode switching button 16 is connected to the system control circuit 21. The user can select a desired observation mode from among the three observation modes by operating the observation mode switching button 16.

Here, the observation mode switching button 16 is an independent operation member, but may be provided in the operation panel (not illustrated) of the video processor 13.

An observation mode signal representing an observation mode selected via the observation mode switching button 16 is inputted to the system control circuit 21. The system control circuit 21 supplies a control signal according to the observation mode signal to the image processing circuit 22.

The image processing circuit 22 generates endoscopic image signals by processing an image pickup signal based on the control signal from the system control circuit 21, and outputs the endoscopic image signals to the monitor 15. In other words, the image processing circuit 22 performs image processing according to an observation mode.

The light source apparatus 14 includes a light source control circuit 31, a plurality of (here, four) light sources 32a, 32b, 32c, 32d, a plurality of (here, four) mirrors 33a, 33b, 33c, 33d, a collecting lens 34, a filter 35 and a filter driving section 36.

The light source control circuit 31 includes a CPU, a ROM and a RAM and controls the respective sections inside the light source apparatus 14 based on a control signal received from the video processor 13 via a signal wire inside the cable 18.

The light source 32a is a light emitting diode (hereinafter referred to as "LED") configured to emit narrow band light having a center wavelength of 410 nm and a full width at half maximum of 10 nm (V-LED). The light source 32a is a light emitting element configured to emit narrow band light of violet. Light emitted from the light source 32a is transmitted through blue parts of the color filter of the image pickup device 12b of the image pickup section 12a. In other words, the light source 32a emits narrow band light NBL1 having a center wavelength of 410 nm.

The light source 32b is an LED configured to emit narrow band light having a center wavelength of 460 nm and a full width at half maximum of 10 nm (B-LED). The light source 32b is a light emitting element configured to emit narrow band light of blue. Light emitted from the light source 32b is transmitted through the blue parts of the color filter of the image pickup device 12b of the image pickup section 12a. In other words, the light source 32b emits narrow band light NBL2 having a center wavelength of 460 nm.

The light source 32c is an LED configured to emit narrow band light having a center wavelength of 540 nm and a full width at half maximum of 30 nm (G-LED). The light source 32c is a light emitting element configured to emit narrow band light of green. Light emitted from the light source 32c is transmitted through green parts of the color filter of the image pickup device 12b of the image pickup section 12a. In other words, the light source 32c emits narrow band light NBL3 having a center wavelength of 540 nm.

The light source 32d is an LED configured to emit narrow band light having a center wavelength of 630 nm and a full width at half maximum of 10 nm (R-LED). The light source 32d is a light emitting element configured to emit narrow band light of red. Light emitted from the light source 32d is transmitted through red parts of the color filter of the image pickup device 12b of the image pickup section 12a. In other words, the light source 32d emits narrow band light NBL4 having a center wavelength of 630 nm.

Although each of the light sources is an LED here, each of all or part of the plurality of light sources may be a combination of a laser diode and a phosphor.

Each of the mirrors 33a, 33b, 33c, 33d (hereinafter, referred to as "mirror 33" when the four mirrors or any arbitrary one of the four mirrors are referred to) is a dichroic mirror.

The mirror 33a is an optical material configured to reflect the narrow band light NBL1 having a center wavelength of 410 nm via a mirror surface inside and transmit light of other wavelengths.

The mirror 33b is an optical material configured to reflect the narrow band light NBL2 having a center wavelength of 460 nm via a mirror surface inside and transmit light of other wavelengths.

The mirror 33c is an optical material configured to reflect the narrow band light NBL3 having a center wavelength of 540 nm via a mirror surface inside and transmit light of other wavelengths.

The mirror 33d is an optical material configured to reflect the narrow band light NBL4 having a center wavelength of 630 nm via a mirror surface inside and transmit light of other wavelengths.

Therefore, the narrow band light NBL1 emitted from the light source 32a is reflected by the mirror 33a and then travels toward the collecting lens 34. The narrow band light NBL2 emitted from the light source 32*b* is reflected by the mirror 33*b* and transmitted by the mirror 33*a* and then travels toward the collecting lens 34. The narrow band light NBL3 emitted from the light source 32*c* is reflected by the mirror 33*c* and transmitted by the mirrors 33*a* and 33*b* and then travels toward the collecting lens 34. The narrow band light NBL4 emitted from the light source 32*d* is reflected by the mirror 33*d* and transmitted by the mirrors 33*a*, 33*b* and 33*c* and then travels toward the collecting lens 34.

The collecting lens 34 collects light from the four mirrors 33*a* to 33*d* on a proximal end face of the light guide inside the light guide cable 19. The light from the collecting lens 34 is outputted from a distal end face of the light guide inside the light guide cable 19 and supplied to the rigid endoscope 11 via the light guide connector 11*d*. The light inputted to the light guide connector 11*d* is outputted as illuminating light from the illumination window at the insertion portion 11*a*.

The filter 35 is disposed on the emission side of the light source 32*c* in such a manner that the filter 35 can be interposed between the light source 32*c* and the mirror 33*c*. The filter 35 transmits only narrow band light NBL31 of a predetermined wavelength band, here, a wavelength band having a center wavelength of 515 nm and a full width at half maximum of 10 nm.

Here, the center wavelength only needs to fall within a range of from 505 nm to 515 nm.

The filter 35 can be moved to either a position on an optical path of light emitted from the light source 32*c* or a position that is off from the optical path by the filter driving section 36.

The filter driving section 36 includes a driving mechanism such as an electromagnetic actuator and changes a position of the filter 35 in response to a control signal from the light source control circuit 31.

In the normal light observation mode and the narrow band light observation mode, as indicated by the solid line in FIG. 1, the filter 35 is moved so as to retract from the position that is off from the optical path of light emitted from the light source 32*c*. In the bleeding point observation mode, as indicated by the alternate long and two short dashes line in FIG. 1, the filter 35 is moved so as to be disposed at the position on the optical path of light emitted from the light source 32*c*.

In the normal light observation mode, current is supplied to the three light sources 32*b*, 32*c*, 32*d* to cause the narrow band light NBL2, the narrow band light NBL3 and the narrow band light NBL4 to be emitted simultaneously from the light source apparatus 14.

In the narrow band light observation mode, current is supplied to the two light sources 32*a*, 32*c* to cause the narrow band light NBL1 and the narrow band light NBL3 to be emitted simultaneously from the light source apparatus 14.

In the bleeding point observation mode, current is supplied to the three light sources 32*b*, 32*c*, 32*d* and the filter 35 is disposed on the emission side of the light source 32*c* to cause the narrow band light NBL2, the narrow band light NBL4 and the narrow band NBL31 having a center wavelength of 515 nm to be emitted simultaneously from the light source apparatus 14.

Here, in the normal light observation mode, current may be supplied also to the light source 32*a* to irradiate a subject with the narrow band light NBL1 together with the aforementioned three types of narrow band light NBL2, NBL3, NBL4.

Figure 2:
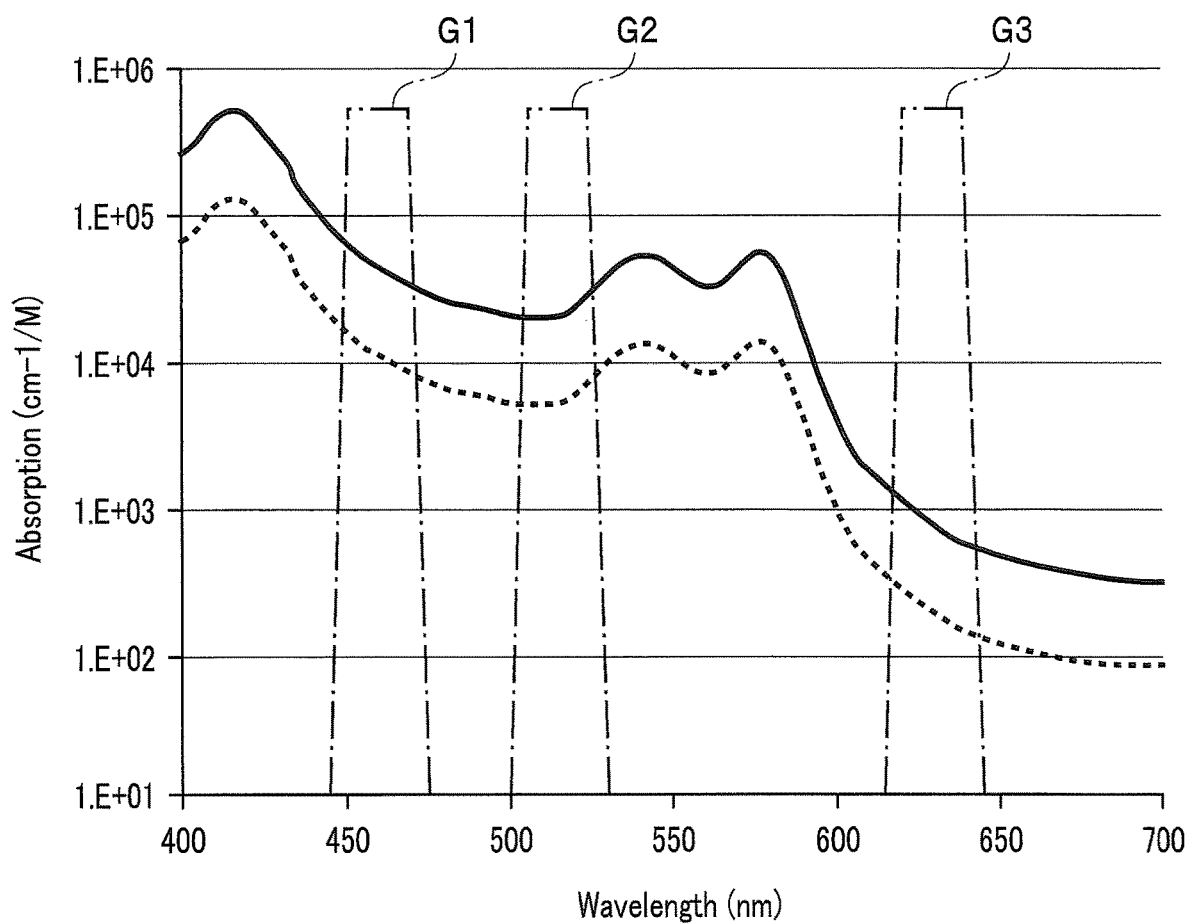
FIG. 2 is a diagram indicating an example of light absorption characteristics of blood and wavelength bands of emitted light from respective light sources in a bleeding point observation mode, according to the first embodiment of the present invention.

FIG. 2 is a diagram illustrating an example of light absorption characteristics of blood and wavelength bands of emitted light from respective light sources in the bleeding point observation mode.

FIG. 2 indicates light absorption characteristics of arterial blood, and the vertical axis in FIG. 2 represents degrees of absorption of light by arterial blood and the horizontal axis represents wavelength bands of each type of light. The solid line indicates a graph of a degree of light absorption by original arterial blood, that is, arterial blood itself, and the dotted line indicates a graph of a degree of light absorption by arterial blood diluted with water. Here, a ratio of oxygenated hemoglobin ($HbO_2$) and deoxygenated hemoglobin (Hb) in the arterial blood is $HbO_2$:Hb=97.5:2.5.

Graph G1 of an alternate long and short dash line indicates an intensity distribution of illuminating light NBL2 of a wavelength band having a center wavelength of 460 nm, graph G2 of an alternate long and short dash line indicates an intensity distribution of illuminating light NBL31 of a wavelength band having a center wavelength of 515 nm, and graph G3 of an alternate long and short dash line indicates an intensity distribution of illuminating light NBL4 of a wavelength band having a center wavelength of 630 nm.

As illustrated in FIG. 2, the original arterial blood and the arterial blood diluted with water are different in light absorption characteristics of hemoglobin in the blood, and in particular, are low in absorption characteristics of the light NBL31 of a wavelength band having a center wavelength of 515 nm as with light of a wavelength band having a center wavelength of 600 nm, which has conventionally been used for displaying bleeding point.

The original arterial blood and the arterial blood diluted with water are different in absorption characteristics of the light NBL2 of a wavelength band having a center wavelength of 460 nm by hemoglobin in the blood, but are generally high in absorption characteristics of the light NBL2 of a wavelength band having a center wavelength of 460 nm. Therefore, an image generated by light of a wavelength band having a center wavelength of 460 nm is dark in its entirety, resulting in a failure to distinguish between an image region of the original arterial blood and an image region of the arterial blood diluted with water.

On the other hand, the original arterial blood and the arterial blood diluted with water are also different in absorption characteristics of the light NBL4 of a wavelength band having a center wavelength of 630 nm by hemoglobin in the blood, but are generally low in absorption characteristics of the light NBL4 of a wavelength band having a center wavelength of 630 nm. Therefore, images generated by the light NBL4 of a wavelength band having a center wavelength of 630 nm are bright in their entireties, resulting in a failure to distinguish between an image region of the original arterial blood and an image region of the arterial blood diluted with water.

As described above, the absorption characteristics of the light NBL31 of a wavelength band having a center wavelength of 515 nm by hemoglobin is not the same as the absorption characteristics of light of a wavelength band having a center wavelength of 600 nm, but is lowered in a manner that is substantially the same as the absorption characteristics of the light of a wavelength band having a center wavelength of 600 nm. However, the absorption characteristics of the light NBL31 of a wavelength band having a center wavelength of 515 nm by hemoglobin is not so low as the absorption characteristics of the light of a wavelength band having a center wavelength of 600 nm.

Therefore, an increase in luminance of an image generated by the light NBL31 of a wavelength band having a center wavelength of 515 nm enables provision of a high contrast image in which an image region of the original arterial blood and an image region of the arterial blood diluted with water can be distinguished from each other.

Figure 3:
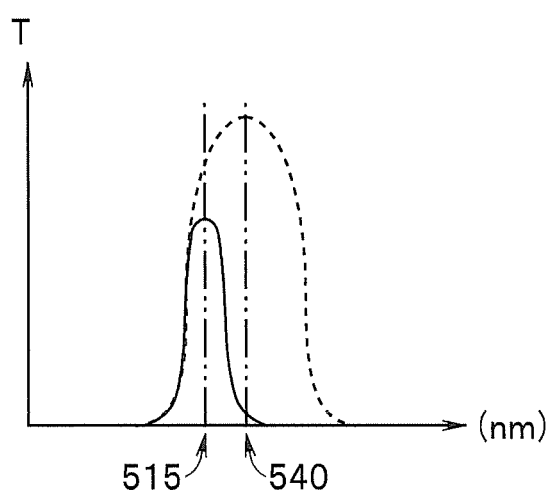
FIG. 3 is a diagram indicating a light transmission characteristic of a filter 35 according to the first embodiment of the present invention.

FIG. 3 is a diagram indicating a light transmission characteristics of the filter 35.

The filter 35 is a filter configured to transmit only the narrow band light NBL31 having a center wavelength of 515 nm in the narrow band light NBL3 having a center wavelength of 540 nm. In FIG. 3, the horizontal axis represents wavelength bands and the vertical axis represents transmittance T.

The light source 32c emits the narrow band light NBL3 having a center wavelength of 540 nm such as indicated by the dotted line in FIG. 3, but if the narrow band light NBL3 is transmitted through the filter 35, the narrow band light NBL31 having a center wavelength of 515 nm and a full width at half maximum of ±10 nm such as indicated by the solid line in FIG. 3 is outputted from the filter 35.

Therefore, light emitted from the light source 32c becomes the narrow band light NBL31 after the light is transmitted through the filter 35.

Here, the filter 35 configured to transmit only the narrow band light NBL31 having a center wavelength of 515 nm is disposed so as to be capable of entering the optical path or retracting from the optical path, between the light source 32c and the mirror 33c; however, as indicated in the alternate long and two short dashes line in FIG. 1, a trimodal filter 37 configured to transmit the narrow band light NBL2, the narrow band light NBL31 and the narrow band light NBL4 may be disposed so as to be capable of entering the optical path from the mirror 33a or retracting from the optical path from the mirror 33a, between the mirror 33a and the collecting lens 34. The trimodal filter 37 is driven by a filter driving section (not illustrated) so as to be disposed between the mirror 33a and the collecting lens 34 in the bleeding point observation mode.

As described above, the light source apparatus 14 includes: the light source 32c, which is a light emitting element configured to emit light of a green wavelength band; the filter 35a configured to transmit only narrow band light NBL31 including a wavelength that is minimally absorbed by blood within the light of the green wavelength band and output the narrow band light NBL31; the light source 32b, which is a light emitting element configured to emit narrow band light NBL2 whose wavelength is shorter and which is more absorbed by blood than the green wavelength band; and the light source 32d, which is a light emitting element configured to emit narrow band light NBL4 whose wavelength is longer and which is less absorbed by blood than the green wavelength band.

Referring back to FIG. 1, the image processing circuit 22 performs processing of an image pickup signal from the image pickup section 12a, according to settings made by a surgeon, which is a user, and the observation mode.

In the normal light observation mode, the image processing circuit 22 processes an image pickup signal from the image pickup section 12a to generate three images of BGR and outputs the three images to three color, B G and R, channels of the monitor 15, and an endoscopic image when a subject is irradiated with white light is thus displayed on the monitor 15. As described above, in the normal light observation mode, the subject is irradiated with light from the three light sources 32b, 32c, 32d.

In the narrow band light observation mode, the image processing circuit 22 processes an image pickup signal from the image pickup section 12a to generate two, B and G, images and outputs the two images to the three color channels of the monitor 15 with the B image allocated to the B and G channels of the monitor 15 and the G image allocated to the R channel, and an endoscopic image when the subject is irradiated with predetermined narrow band light is thus displayed on the monitor 15. As described above, in the narrow band light observation mode, the subject is irradiated with light from the two light sources 32a, 32c.

In the bleeding point observation mode, the image processing circuit 22 processes an image pickup signal from the image pickup section 12a to generate three, B, G and R, images and outputs the three images to the three color channels of the monitor 15 with the B image allocated to the B channel of the monitor 15, the G image allocated to the G channel and the R image allocated to the R channel of the monitor 15, and an endoscopic image with a bleeding point highlighted is displayed on the monitor 15. As described above, in the bleeding point observation mode, the subject is irradiated with light from the three light sources 32b, 32c, 32d, but light from the light source 32c is made to be the narrow band light NBL31 having a center wavelength of 515 nm by the filter 35 and is then applied to the subject.

Since the image processing in each of the normal light observation mode and the narrow band light observation mode is publicly known, here, the image processing in the bleeding point observation mode will be described.

Figure 4:
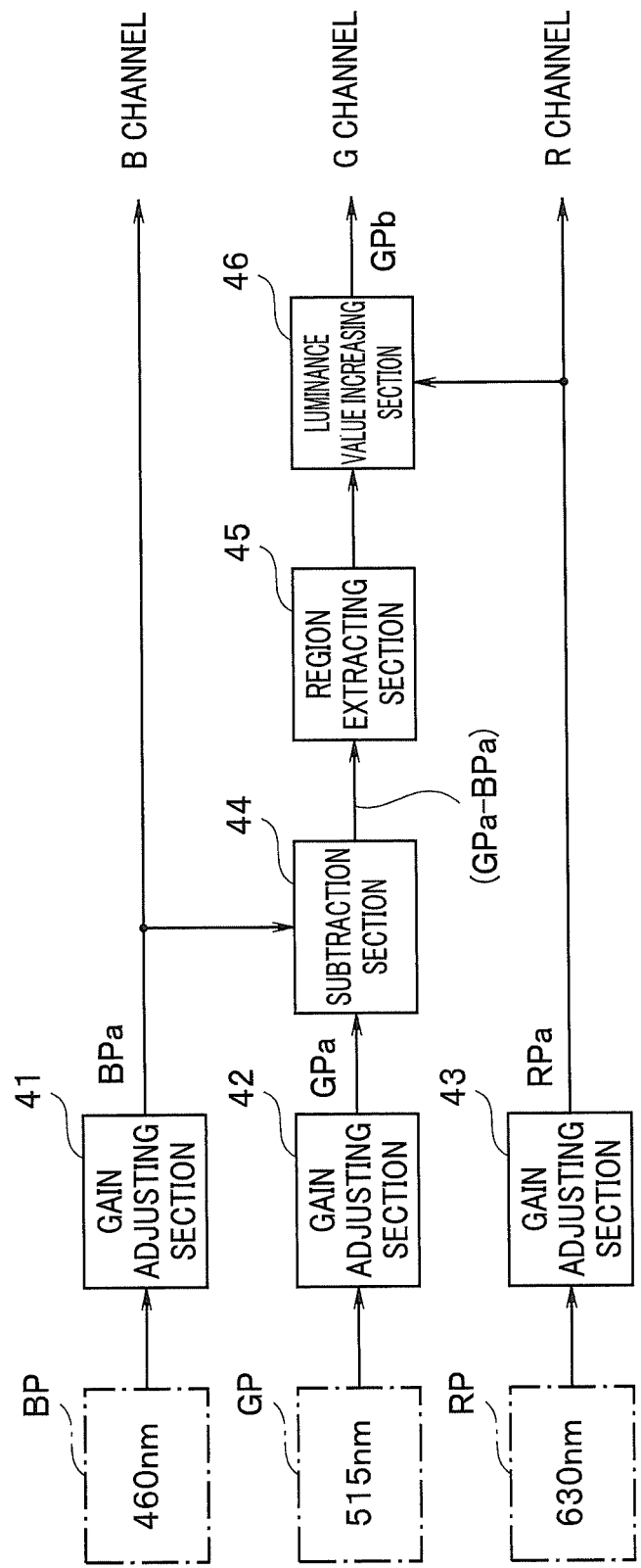
FIG. 4 is a block diagram of an image processing section for the bleeding point observation mode in the image processing circuit according to the first embodiment of the present invention.

FIG. 4 is a block diagram of an image processing section for the bleeding point observation mode in the image processing circuit. FIG. 4 illustrates processing blocks for the bleeding point observation mode alone and illustration of processing blocks, etc., for other observation modes is omitted.

In the image processing circuit 22, three images BP, GP, RP corresponding to blue, green and red color filters in the color filter in the image pickup section 12a are generated from the image pickup signal from the image pickup section 12a.

The first image BP corresponding to the blue color filter is an image generated from reflected light of the narrow band light NBL2 having a center wavelength of 460 nm.

The second image GP corresponding to the green color filter is an image generated from reflected light of the narrow band light NBL31 having a center wavelength of 515 nm.

The third image RP corresponding to the red color filter is an image generated by reflected light of the narrow band light NBL4 having a center wavelength of 630 nm.

The image processing circuit 22 includes three gain adjusting sections 41, 42, 43, a subtraction section 44, a region extracting section 45 and a luminance value increasing section 46.

The gain adjusting sections 41, 42, 43 are circuits configured to adjust luminances of the first image BP, the second image GP and the third image RP according to the observation mode, respectively. In the gain adjusting section 41, 42, 43, luminances of two or three images from among the first image BP, the second image GP and the third image RP are adjusted so as to have respective average luminance values that are substantially equal to each other. The gain adjusting sections 41, 42, 43 output a first image BPa, a second image GPa and a third image RPa with the luminances adjusted, respectively.

The subtraction section 44 is a circuit configured to subtract the first image BPa from the second image GPa and output a differential image (GPa–BPa) for the second image GPa and the first image BPa. The differential image (GPa–BPa) is generated by subtracting pixel values of respective pixels in the first image GPa from pixel values of the corresponding pixels in the second image GPa.

The differential image (GPa–BPa) indicates a difference between the first image BPa and the second image GPa. A degree of the difference between the first image BPa and the second image GPa is represented by differences between respective pixels in an image signal of the first image BPa and respective corresponding pixels in an image signal of the second image GPa.

The region extracting section 45 receives an input of an image signal obtained as a result of forming an image of a subject irradiated with the narrow band light NBL31 including a wavelength that is minimally absorbed by blood within the green wavelength band, the image of the subject including a bleeding point, and extracts a blood pool region having a blood concentration that is lower than a blood concentration of the bleeding point in a region representing blood in the image signal.

Here, the region extracting section 45 is a circuit configured to extract a region including pixels each having a pixel value that is equal to or exceeds a predetermined pixel value from the differential image from the subtraction section 44.

In other words, the region extracting section 45 receives an input of an image signal including a plurality of pixels as the image signal of the first image BPa, receives an input of an image signal including a plurality of pixels as the image signal of the second image GPa, calculates degrees of difference representing differences between respective pixels in the image signal of the second image GPa and the respective corresponding pixels in the image signal of the first image BPa on a pixel-by-pixel basis, and extracts a region of pixels, the respective degrees of difference for the pixels exceeding a threshold value for extracting a blood pool region in the region representing blood, as a blood pool region.

The luminance value increasing section 46 configures a luminance value raising section configured to raise a luminance value of the blood pool region in the second image GPa.

Here, the luminance value increasing section 46 is a circuit configured to increase pixel values, that is, luminance values of an image of the region extracted by the region extracting section 45 (hereinafter referred to as "extracted region image") so as to be substantially equal to luminance values of a region in the third image RPa, the region corresponding to the extracted region ER.

Although the extracted region ER is extracted by subtraction processing performed by the subtraction section 44 here, the extracted region ER may be extracted through determination of whether or not a ratio between pixel values of pixels corresponding to each other is equal to or exceeds or equal to or below a predetermined value by division processing.

The first image BPa subjected to the gain adjustment in the gain adjusting section 41 is allocated to the blue (B) channel of the monitor 15.

A combined image GPb formed by combination of the image of the extracted region ER with the luminance value increased by the luminance value increasing section 46 and an image of a region other than the extracted region ER in the second image GPa is allocated to the green (G) channel of the monitor 15.

As described above, the narrow band light NBL31 having a center wavelength of 515 nm is more absorbed than the narrow band light having a center wavelength of 600 nm as illustrated in FIG. 2, and thus causes an image of a region of blood mixed with water to be darken. Therefore, the pixel values of the plurality of pixels of the extracted region ER in the second image GPa are increased by the luminance value increasing section 46.

In other words, the luminance value increasing section 46 generates a pseudo-image of an extracted region using narrow band light having a center wavelength of 600 nm by increasing the luminance values of the plurality of pixels of the extracted region ER in the second image GPa.

The third image RPa subjected to the gain adjustment by the gain adjusting section 43 is allocated to the red (R) channel of the monitor 15.

In other words, the gain adjusting sections 41, 43 and the luminance value increasing section 46 configure an image generating section configured to generate image signals in which the image signal of the first image BPa, the image signal of the combined image GPb and the image signal of the third image RPa are allocated to respective different colors.

Figure 5:
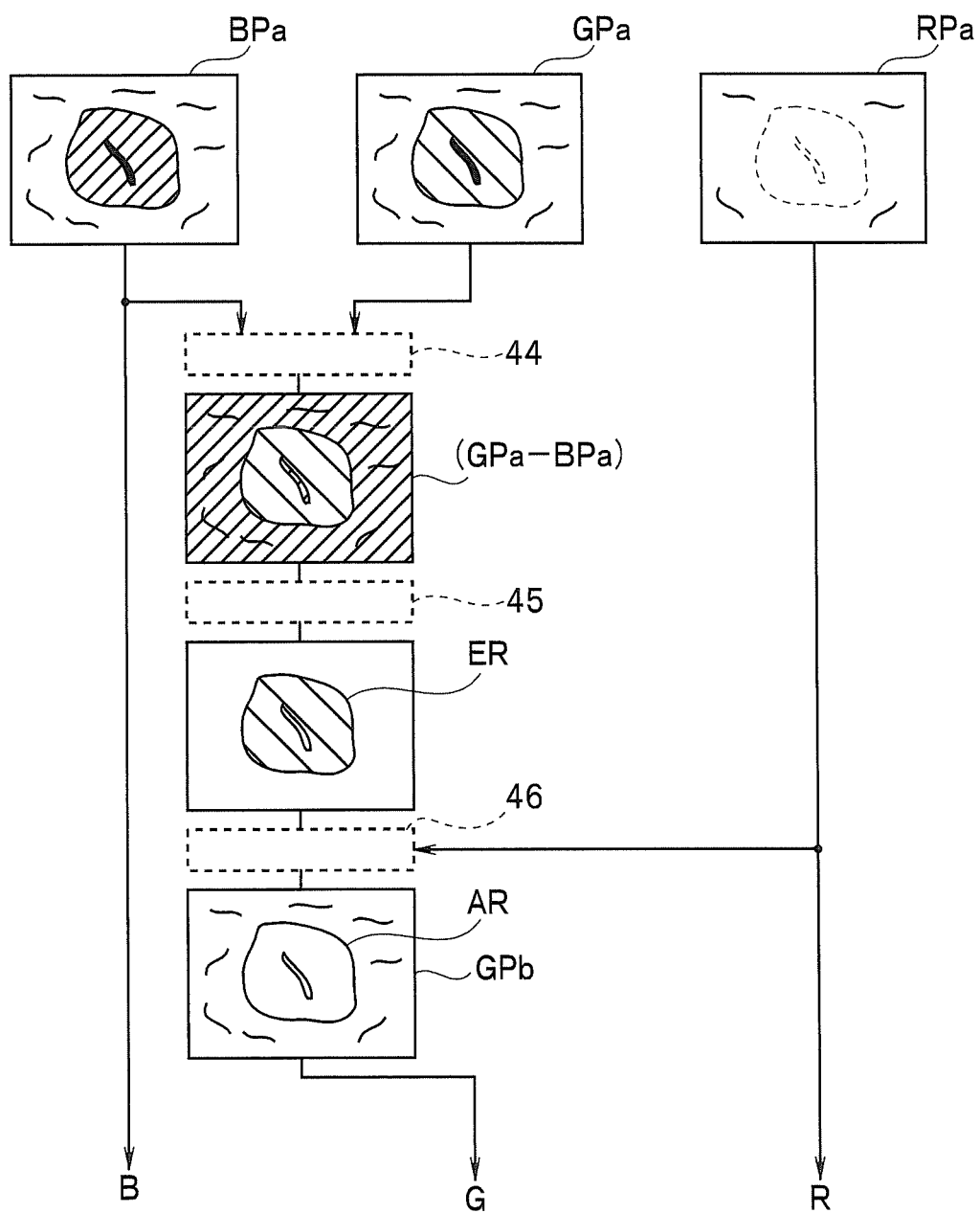
FIG. 5 is a diagram for describing changes of an image generated by processing in an image processing circuit 22, according to the first embodiment of the present invention.

FIG. 5 is a diagram for describing changes of an image generated by processing in the image processing circuit 22.

From among the first, second and third images BPa, GPa, RPa subjected to the gain adjustment by the three gain adjusting sections 41, 42, 43, the second image GPa and the first image BPa are subjected to subtraction processing by the subtraction section 44 to generate a differential image (GPa–BPa).

The differential image (GPa–BPa) is inputted to the region extracting section 45, and the region extracting section 45 determines whether or not a pixel value of each pixel in the differential image P21 is equal to or exceeds a predetermined threshold value to obtain an extracted region ER.

The luminance value increasing section 46 generates a region image AR with only pixel values of a plurality of pixels in the extracted region ER increased so as to be substantially equal to pixel values, for example, an average value of the pixel values of a plurality of pixels in a region in the third image RPa, the region corresponding to the extracted region ER. Furthermore, the luminance value increasing section 46 generates and outputs a combined image GPb obtained by combining the generated region image AR and an image of a region other than the extracted region ER in the second image GPa. In other words, pixel values of pixels in a region other than the extracted region ER in the combined image GPb remain uncorrected and are equal to pixel values of pixels in the second image GPa.

An image signal of the first image BPa is allocated to the blue (B) channel of the monitor 15, an image signal of the combined image GP2b is allocated to the green (G) channel of the monitor 15 and an image signal of the third image RPa is allocated to the red (R) channel of the monitor 15, and the image signals are outputted to the monitor 15.

As described above, the video processor 13 generates, from an image pickup signal outputted by the image pickup device 12b upon receipt of reflected light from a subject irradiated with the narrow band light NBL31 having a center wavelength of 515 nm, the wavelength band NBL2 having a center wavelength of 460 nm and the wavelength band NBL4 having a center wavelength of 630 nm, an image signal of a second image GPa of the subject irradiated with the narrow band light NBL31, the second image GPa of the subject including a bleeding point in a region representing blood, an image signal of a first image BPa of the subject irradiated with the wavelength band NBL2 and an image signal of a third image RPa of the subject irradiated with the wavelength band NBL4, extracts a blood pool region having a blood concentration that is lower than a blood concentration of the bleeding point in the image signal of the second image GPa, raises a luminance value of the extracted blood pool region and outputs the image signal of the first image BPa, an image signal of a combined image GPb and the image signal of the third image RPa.

Figure 6:
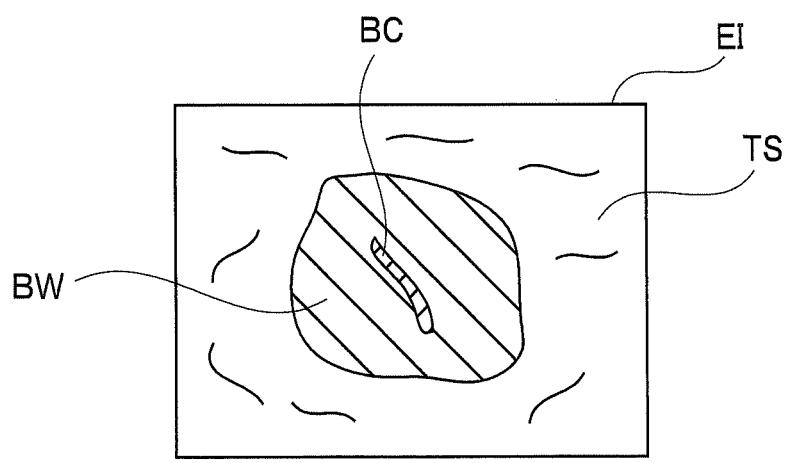
FIG. 6 is a diagram illustrating example display of an endoscopic image displayed on a monitor 15 in the bleeding point observation mode, according to the first embodiment of the present invention.

FIG. 6 is a diagram illustrating example display of an endoscopic image displayed on the monitor 15 in the bleeding point observation mode. Upon the endoscope apparatus 1 being brought into the bleeding point observation mode to observe a mucous surface partially covered by blood, an endoscopic image EI such as illustrated in FIG. 6 is displayed on the monitor 15.

In the bleeding point observation mode, pixel values of the extracted region ER are increased by the luminance value increasing section 46, and thus, a region BW becomes yellow without becoming red, and thus, in the endoscopic image EI displayed on the monitor 15, a bleeding point region BC is displayed in red, the region BW in which blood, water, etc., are mixed is displayed in yellow, and a mucous tissue region TS not covered by blood is displayed in white.

If the pixel values of the extracted region ER are not increased, the region BW in which blood, water, etc., are mixed also becomes reddish and lacks contrast with the bleeding point region BC.

Therefore, in the bleeding point observation mode, a user can clearly view the bleeding point region BC in the mucous surface covered by blood.

Also, since a subject image can be picked up by means of simultaneous illumination using narrow band light with a center wavelength of 515 nm rather than 600 nm and the image pickup device 12b including a color filter, as opposed to the case of a conventional frame-sequential image pickup method, no color shift occurs in an endoscopic image.

Next, modifications will be described.
(Modification 1)

Although in the above-described embodiment, the luminance value increasing section subjects a second image GPa to luminance value increase processing, the luminance value increasing section may be configured to subject a first image BPa to luminance value increase processing.

Description of modification 1 will be given below only on components that are different from the components in the above-described embodiment.

Figure 7:
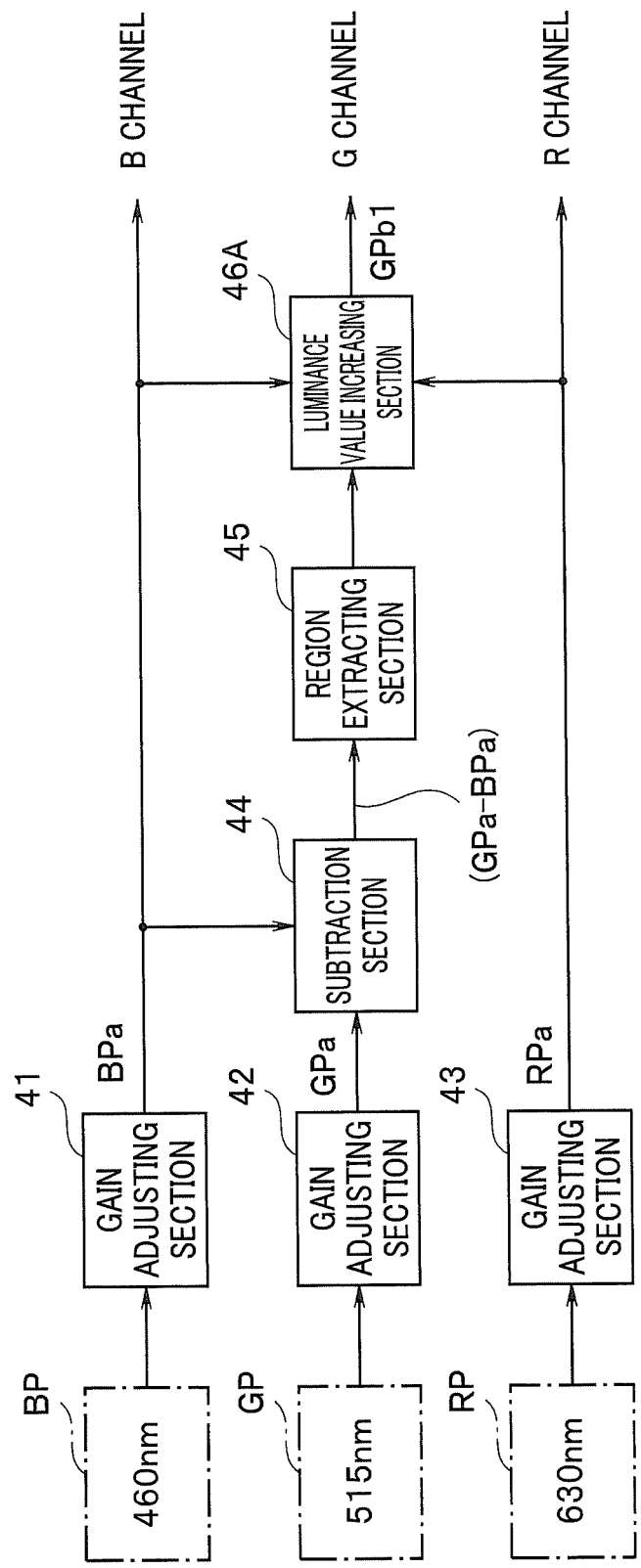
FIG. 7 is a block diagram of an image processing section for a bleeding point observation mode in an image processing circuit 22 according to modification 1 of the first embodiment of the present invention.
Figure 8:
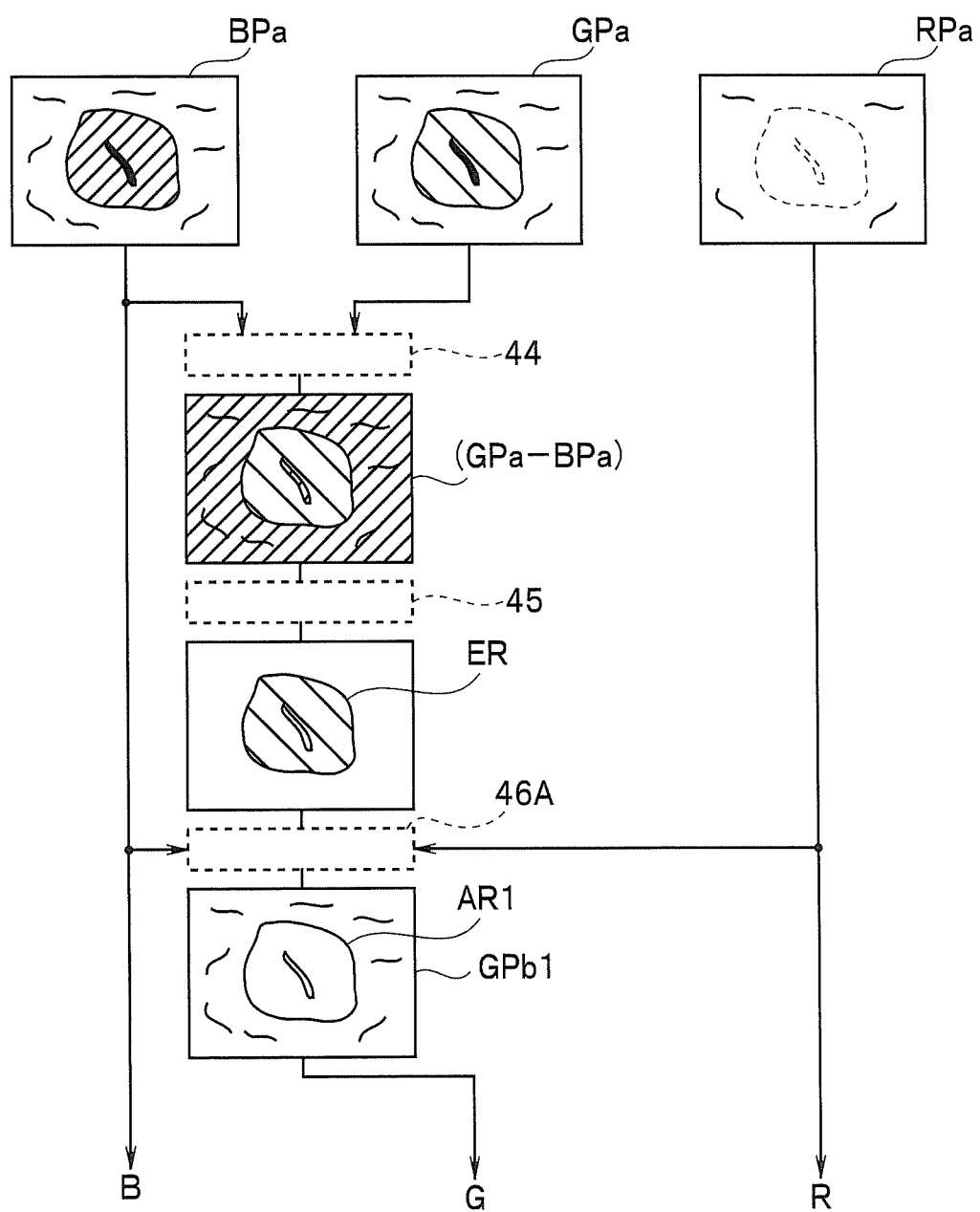
FIG. 8 is a diagram for describing image processing in the image processing circuit 22 according to modification 1 of the first embodiment of the present invention.

FIG. 7 is a block diagram of an image processing section for a bleeding point observation mode in an image processing circuit according to modification 1. FIG. 8 is a diagram for describing image processing in the image processing circuit 22 according to modification 1.

A luminance value increasing section 46A generates a region image AR1 with only pixel values of an extracted region ER in a first image BPa increased so as to be substantially equal to pixel values, for example, an average value of pixel values of a plurality of pixels in a region in a third image RPa, the region corresponding to the extracted region ER. Furthermore, the luminance value increasing section 46A generates and outputs a combined image GPb1 obtained by combining the region image AR1 with the pixel values increased in the first image BPa and an image of a region other than the extracted region ER in the second image GPa. In other words, in the combined image GPb1, pixel values of pixels in the region other than the extracted region ER remain uncorrected and are equal to pixel values of pixels in the second image GPa.

In other words, the luminance value increasing section 46A increases luminance values of a blood pool region in an image signal of a subject irradiated with second narrow band light NBL2 whose wavelength is shorter and which is more absorbed by blood than narrow band light NBL31.

As illustrated in FIG. 2, the narrow band light NBL2 having a center wavelength of 460 nm is more absorbed than the narrow band light NBL31 having a center wavelength of 515 nm, and luminance values of the region image AR1 in the first image BPa are thus lower, and therefore, gains of the luminance value increasing section 46A are larger than gains in the above-described embodiment.

Modification 1 also enables provision of effects that are similar to the effects of the above-described embodiment.
(Modification 2)

Although in modification 1, the luminance value increasing section 46A subjects a first image BPa to luminance value increase processing, the luminance value increasing section may configured to replace an image of an extracted region ER in a second image GPa with an image of a region in a third image RPa, the region corresponding to the extracted region ER.

Description of modification 2 will be given below only on components that are different from the components in the above-described embodiment.

Figure 9:
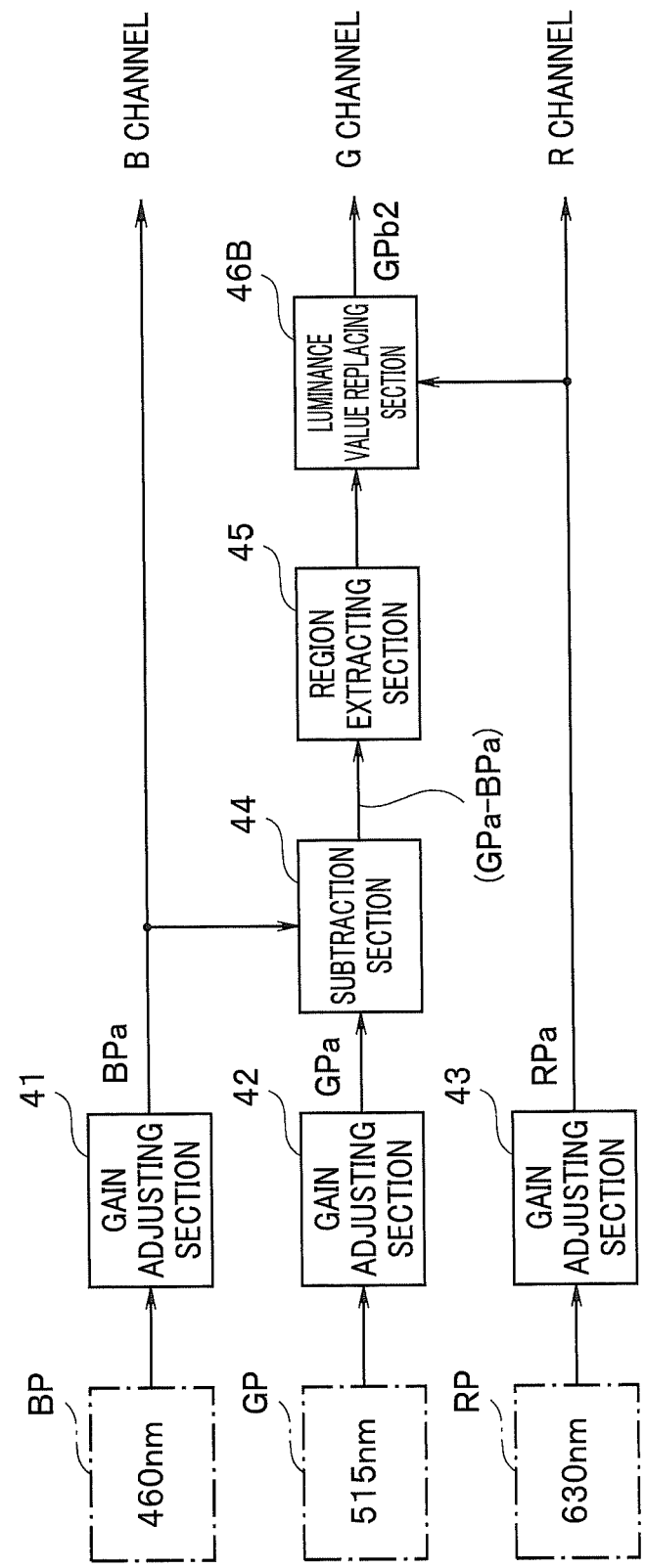
FIG. 9 is a block diagram of an image processing section for a bleeding point observation mode in an image processing circuit 22 according to modification 2 of the first embodiment of the present invention.
Figure 10:
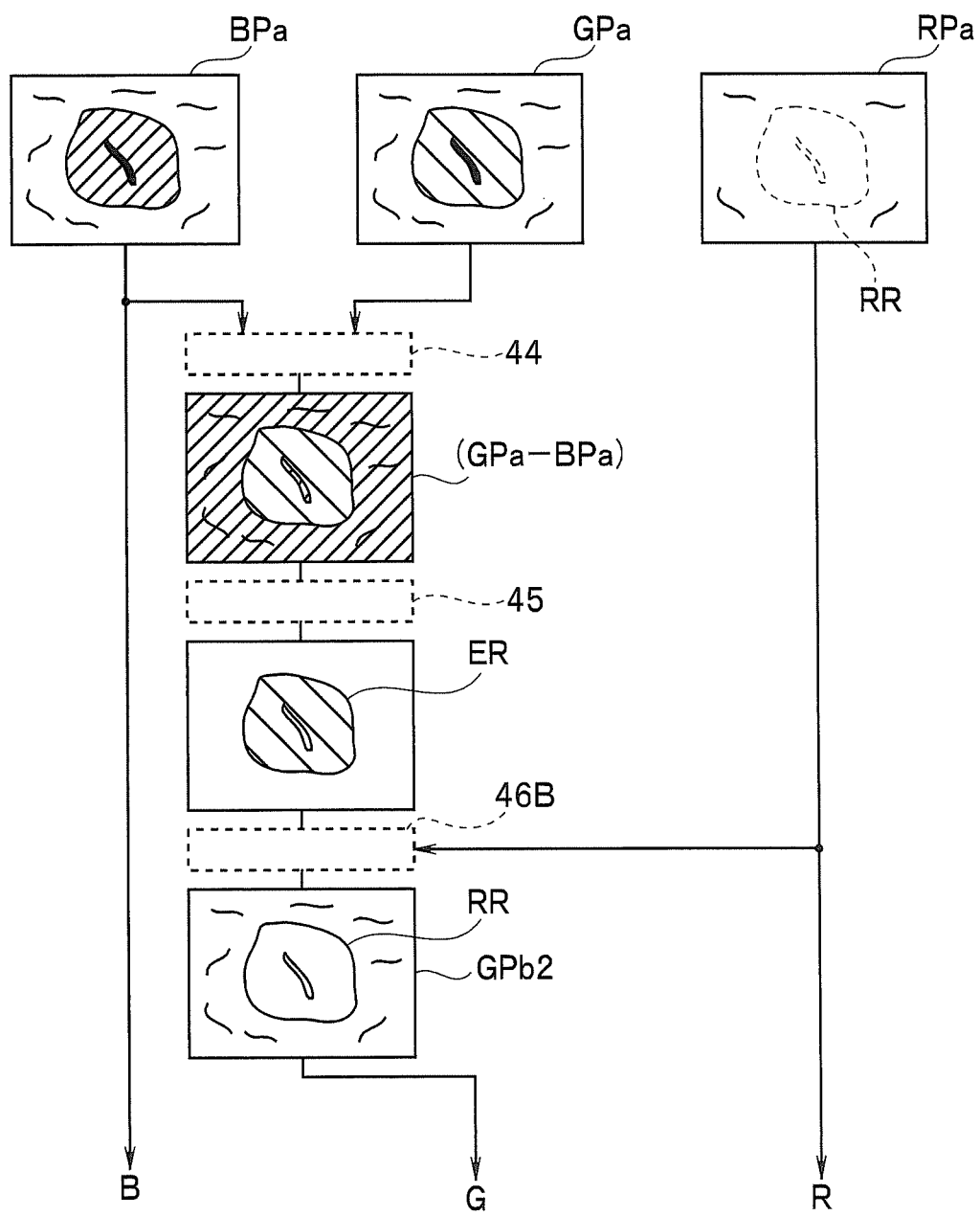
FIG. 10 is a diagram for describing image processing in the image processing circuit 22 according to modification 2 of the first embodiment of the present invention.

FIG. 9 is a block diagram of an image processing section for a bleeding point observation mode in an image processing circuit according to modification 2. FIG. 10 is a diagram for describing image processing in the image processing circuit 22 according to modification 2.

An output of a subtraction section 44 is connected to a luminance value replacing section 46B instead of the luminance value increasing section 46A. An output of the luminance value replacing section 46B is allocated to a green (G) channel of a monitor 15.

The luminance value replacing section 46B performs processing for replacing an extracted region ER in a second image GPa with a plurality of pixels in a region RR in a third image RPa, the region RR corresponding to the extracted region ER. In other words, the extracted region ER in the second image GPa is replaced with the plurality of pixels in the region RR corresponding to the extracted region ER in the third image RPa.

Furthermore, the luminance value replacing section 46B generates and outputs a combined image GPb2 obtained by combining an image of the region RR and an image of a region other than the extracted region ER in the second image GPa. In other words, in the combined image GPb2, pixel values of pixels in the region other than the extracted region ER remain uncorrected and are equal to pixel values of pixels in the second image GPa.

As a result of the image of the extracted region ER in the second image GPa being replaced with the region RR in the third image RPa, luminance values of the extracted region ER in the second image GPa increases.

In other words, the luminance value replacing section 46B configures a luminance value raising section configured to raise luminance values of a blood pool region by replacing luminance values of a blood pool region in an image signal of a second image GPa with luminance values of a blood pool region in an image signal of a third image RPa of a subject irradiated with narrow band light NBL4 whose wavelength is longer and which is less absorbed by blood than narrow band light NBL31.

Modification 2 also enables provision of effects that are similar to the effects of the above-described embodiment.

As described above, the above-described embodiment and the respective modifications each enable provision of an image processing apparatus capable of providing display on a monitor in such a manner that a site causing bleeding, that is, a bleeding point can clearly be viewed when a mucous surface is covered by blood, using a wavelength band other than a range of from 585 nm to 615 nm.

In particular, for example, where a light emitting element such as an LED configured to emit narrow band light having a center wavelength of 600 nm is used as in conventional methods, such light emitting element needs to be additionally provided in a light source apparatus, which is problematic in cost.

Furthermore, for example, where a light emitting element such as an LED configured to emit narrow band light having a center wavelength of 600 nm is used, an image sensor including an on-chip color filter needs to employ what is called a frame-sequential method as an illumination method in order to distinguish between reflected light of narrow band light of 600 nm and reflected light of narrow band light of 630 nm, and thus has a problem of what is called color shift occurring in a displayed image and also has a problem of impossibility of raising a frame rate.

However, according to the above-described embodiment and the respective modifications, no light emitting element for viewing a bleeding region is added to the light source apparatus. Furthermore, what is called simultaneous method is employed as an illumination method, enabling not only preventing color shift from occurring in an endoscopic image but also raising a frame rate.

Second Embodiment

Although in the above-described first embodiment, the image pickup device 12b is an image sensor including an on-chip color filter, in the present embodiment, an image sensor in an image pickup section 12a is a monochrome image sensor including no color filter.

Since an endoscope apparatus 1A according to the second embodiment has a configuration that is substantially the same as the configuration of the endoscope apparatus 1 according to the first embodiment illustrated in FIG. 1, the second embodiment will be described with reference to FIG. 1. Therefore, in the below description, components that are the same as the components in the endoscope apparatus 1 according to the first embodiment are provided with reference numerals that are the same as the reference numerals of the endoscope apparatus 1 and description of such components will be omitted, and only components in the endoscope apparatus 1A according to the second embodiment that are different from the components in the endoscope apparatus 1 according to the first embodiment will be described.

An image pickup device 12b in an image pickup section 12a of an endoscope apparatus 1A according to the second embodiment is a monochrome image sensor including no on-chip color filter. Therefore, the endoscope apparatus 1A according to the second embodiment has a configuration that is similar to the configuration of the endoscope apparatus 1 illustrated in FIG. 1, but is different from the endoscope apparatus 1 according to the first embodiment in that the image pickup device 12b of the image pickup section 12a is a monochrome image sensor.

According to an observation mode, a system control circuit 21 drives a plurality of light sources used in the observation mode in a predetermined order. An image processing circuit 22 obtains and combines a plurality of frame images according to the observation mode and outputs the resulting image signals to a monitor 15. As a result, an endoscopic image according to the observation mode is displayed on the monitor 15.

In each observation mode, a subject is irradiated with illuminating light in a frame-sequential method.

In a normal light observation mode, light sources 32b, 32c, 32d are driven sequentially, and the image processing circuit 22 acquires an image BP of narrow band light NBL2 having a center wavelength of 460 nm, an image GP of narrow band light NBL3 having a center wavelength of 540 nm and an image RP of narrow band light NBL4 having a center wavelength of 630 nm in a predetermined order.

In a narrow band light observation mode, light sources 32a and 32c are driven alternately, and the image processing circuit 22 acquires an image of narrow band light NBL1 having a center wavelength of 410 nm and an image GP of the narrow band light NBL3 having a center wavelength of 540 nm alternately.

In a bleeding point observation mode, a filter 35 is driven and the light sources 32b, 32c, 32d are driven sequentially, and thus a light source apparatus 14 emits the narrow band light NBL2 having a center wavelength of 460 nm, narrow band light NBL31 having a center wavelength of 515 nm and the narrow band light NBL4 having a center wavelength of 630 nm in a predetermined order.

The image processing circuit 22 acquires an image BP of the narrow band light NBL2 having a center wavelength of 460 nm, an image GP of the narrow band light NBL31 having a center wavelength of 515 nm and an image RP of the narrow band light NBL4 having a center wavelength of 630 nm in a predetermined order and performs the processing described in the first embodiment.

In each mode, an endoscopic image is generated from the plurality of images acquired, and image signals of the endoscopic image are outputted to the monitor 15.

In the bleeding point observation mode, an endoscopic image that is similar to the endoscopic image in the first embodiment can be obtained from the acquired three images BP, GP, RP by the processing illustrated in FIGS. 4 and 5 being performed.

Therefore, the endoscope apparatus 1A according to the present embodiment enables provision of effects that are similar to the effects of the first embodiment although not a simultaneous method but a method that is similar to what is called a frame-sequential method is employed as an illumination method.

Furthermore, in the present embodiment, a monochrome image sensor is used, and thus, the number of pixels per frame can be increased, enabling provision of a higher resolution endoscopic image.

Also, each of modifications 1, 2 of the first embodiment can be applied also to the present embodiment.

Third Embodiment

Although in the first embodiment, narrow band light NBL31 having a center wavelength of 515 nm is obtained using the filter 35 and applied to a subject, in the present embodiment, a light emitting element configured to emit narrow band light having a center wavelength of 515 nm is added to a light source apparatus 14 and in a bleeding point observation mode, the light emitting element configured to emit narrow band light having a center wavelength of 515 nm is driven.

An endoscope apparatus according to the third embodiment has a configuration that is substantially the same as the configuration of the endoscope apparatus 1. Therefore, in the below description, components that are the same as the components in the endoscope apparatus 1 according to the first embodiment are provided with reference numerals that are the same as the reference numerals of the endoscope apparatus 1 and description of such components will be omitted, and only components in the endoscope apparatus according to the third embodiment that are different from the components in the endoscope apparatus 1 according to the first embodiment will be described.

Figure 11:
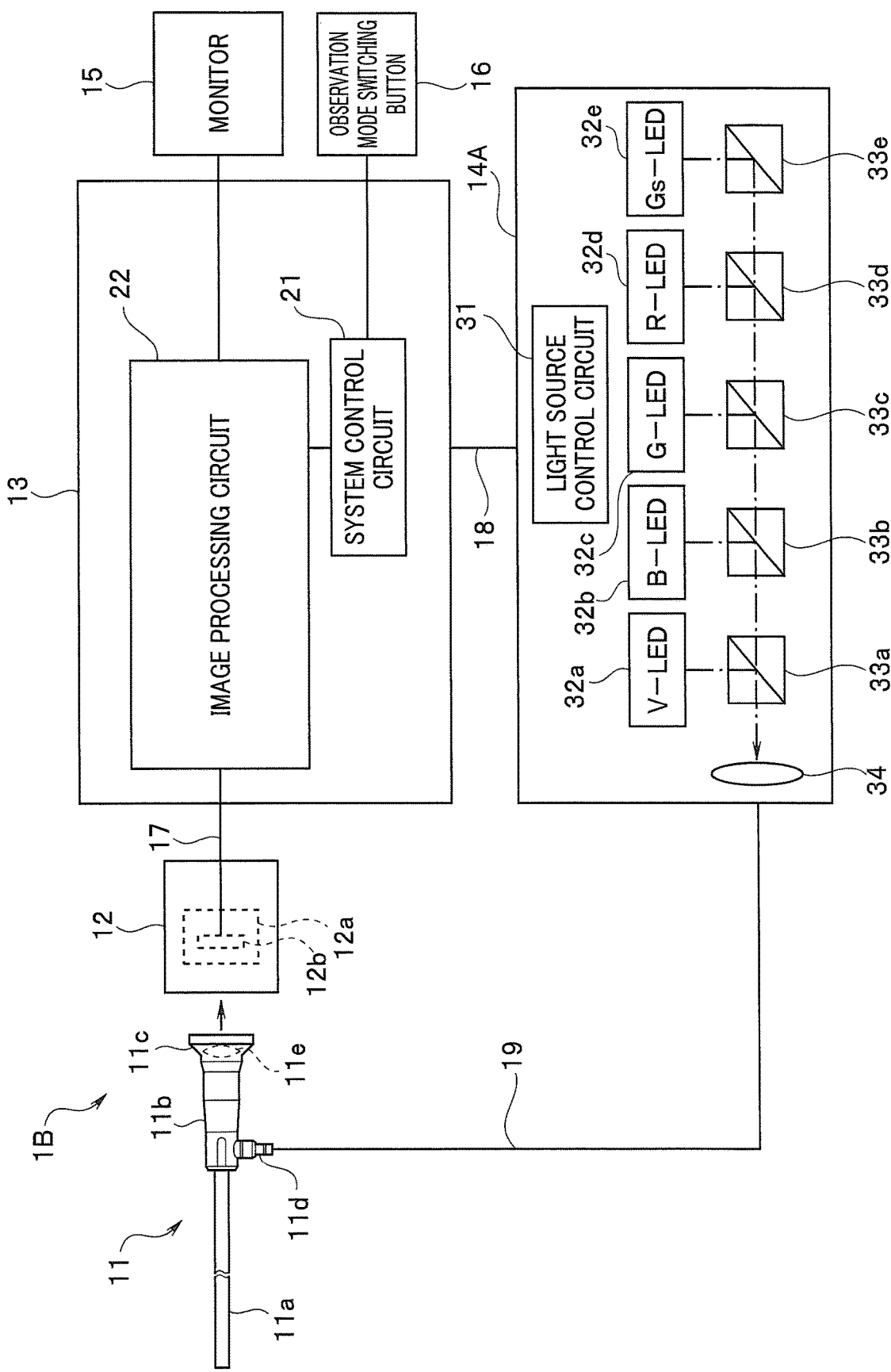
FIG. 11 is a configuration diagram illustrating a configuration of an endoscope apparatus including an image processing apparatus according to a third embodiment of the present invention.

FIG. 11 is a configuration diagram illustrating a configuration of an endoscope apparatus including an image processing apparatus according to the third embodiment.

A light source apparatus 14A in an endoscope apparatus 1B according to the third embodiment includes an LED (Gs-LED) light source 32e, which is a light emitting element configured to emit narrow band light NBL31 having a center wavelength of 515 nm in addition to light sources 32a to 32d, and also includes a mirror 33e for the light source 32e.

The mirror 33e is an optical material configured to reflect the narrow band light NBL31 having a center wavelength of 515 nm via a mirror surface inside and transmit light of other wavelengths.

Also, the filter 35 (or 36) illustrated in FIG. 1 is not provided in the light source apparatus 14A.

In a normal light observation mode, current is supplied to the three light sources 32b, 32c, 32d, and narrow band light NBL2 having a center wavelength of 460 nm, narrow band light NBL3 having a center wavelength of 540 nm and narrow band light NBL4 having a center wavelength of 630 nm are simultaneously emitted from the light source apparatus 14A.

In a narrow band light observation mode, current is supplied to the two light sources 32a, 32c and narrow band light NBL1 having a center wavelength of 410 nm and the narrow band light NBL3 having a center wavelength of 540 nm are simultaneously emitted from the light source apparatus 14.

In a bleeding point observation mode, current is supplied to the three light sources 32b, 32d, 32e, and the narrow band light NBL2 having a center wavelength of 460 nm, the narrow band light NBL4 having a center wavelength of 630 nm and the narrow band light NBL31 having a center wavelength of 515 nm are simultaneously emitted from the light source apparatus 14.

Operation of the image processing circuit 22 is similar to the operation of the image processing circuit 22 in the first embodiment.

Here, the image pickup device 12b includes an on-chip color filter.

In other words, the endoscope apparatus 1B according to the present embodiment is an endoscope apparatus having the normal light observation mode and the bleeding point observation mode, the endoscope apparatus including an endoscope including a rigid endoscope 11 and a camera head 12 including an image pickup device 12b, a video processor 13 and the light source apparatus 14A.

The light source apparatus 14A includes the light source 32c, which is a light emitting element configured to emit narrow band light NBL3 of a green wavelength band, the light source 32b, which is a light emitting element configured to emit narrow band light NBL2 whose wavelength is shorter and which is more absorbed by blood than the green wavelength band, and the light source 32d, which is a light emitting element configured to emit narrow band light NBL4 whose wavelength is longer and which is less absorbed by blood than the green wavelength band, and the light source 32e, which is a light emitting element configured to emit narrow band light NBL31 including a wavelength that is minimally absorbed by blood within light of the green wavelength band.

In the normal light observation mode, the video processor 13 generates three, first, second and third, image signals from an image pickup signal outputted from the image pickup device 12b upon receipt of reflected light from the subject irradiated with the narrow band light NBL2, the narrow band light NBL3 and the narrow band light NBL4, and outputs the three image signals, and in the bleeding point observation mode, the video processor 13 generates a fourth image signal of the subject irradiated with narrow band light NBL31, the fourth image signal of the subject including a bleeding point in a region representing blood, a second image signal and a third image signal from an image pickup signal outputted by the image pickup device 12b upon receipt of reflected light from the subject irradiated with the narrow band light NBL2, the narrow band light NBL31 and the narrow band light NBL4, and extracts a blood pool region having a blood concentration that is lower than a blood concentration of the bleeding point in the fourth image signal and raises luminance values of the extracted blood pool region, and outputs the second image signal, the third image signal and the fourth image signal.

As described above, the above embodiment enables provision of an image processing apparatus capable of providing display on a monitor in such a manner that a site causing bleeding, that is, a bleeding point can clearly be viewed when a mucous surface is covered by blood, using a wavelength band other than the range of from 585 nm to 615 nm.

Furthermore, what is called a simultaneous method is employed as an illumination method, enabling not only preventing color shift from occurring in an endoscopic image but also raising a frame rate.

Also, each of modifications 1, 2 of the first embodiment can be applied also to the present embodiment.

Still furthermore, in the present embodiment, also, image processing such as in the second embodiment may be performed with a monochrome image sensor used as an image sensor in the image pickup section 12a and what is called a frame-sequential method employed as an illumination method as described in the second embodiment.

Fourth Embodiment

Although each of the light source apparatuses according to the first to third embodiments described above uses light emitting elements as light sources, a light source apparatus according to the present embodiment use a lamp configured to emit white light and a trimodal filter.

An endoscope apparatus according to the fourth embodiment has a configuration that is substantially the same as the configuration of the endoscope apparatus 1 according to the first embodiment. Therefore, in the below description, components that are the same as the components in the endoscope apparatus 1 according to the first embodiment are provided with reference numerals that are the same as the reference numerals of the endoscope apparatus 1 and description of such components will be omitted, and only components in the endoscope apparatus according to the fourth embodiment that are different from the components in the endoscope apparatus 1 according to the first embodiment will be described.

Figure 12:
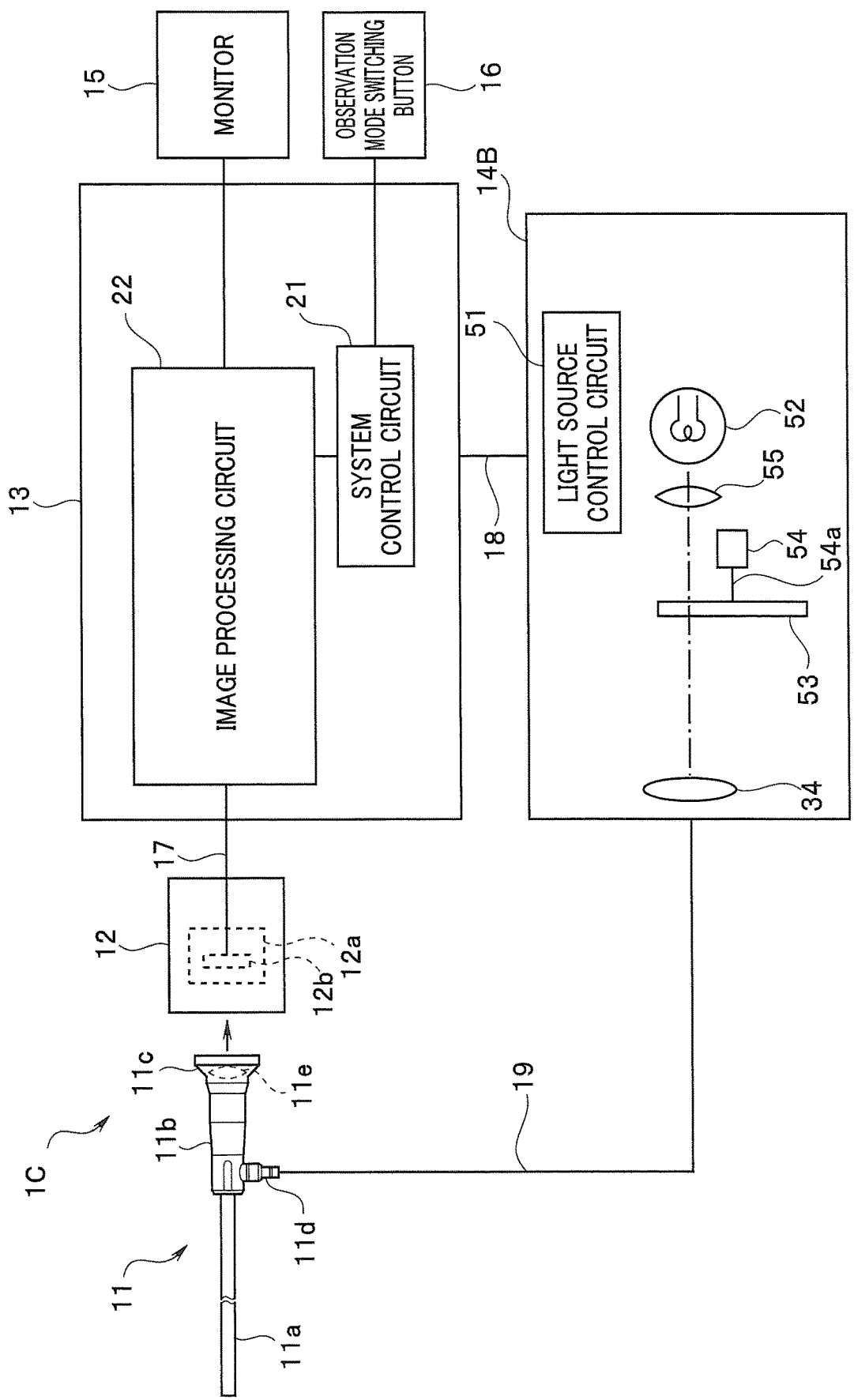
FIG. 12 is a configuration diagram illustrating a configuration of an endoscope apparatus 1C including an image processing apparatus according to a fourth embodiment of the present invention.

FIG. 12 is a configuration diagram illustrating a configuration of an endoscope apparatus 1C including an image processing apparatus according to the fourth embodiment.

A light source apparatus 14B in an endoscope apparatus 1C according to the fourth embodiment includes a collecting lens 34, a light source control circuit 51, a lamp 52, a filter 53, a motor 54 configured to drive the filter 53, and a lens 55.

The light source control circuit 51 controls operation of the filter 53 according to an observation mode.

The lamp 52 is a xenon lamp, which is a light source, and is configured to emit white light.

The filter 53 has a rotary filter having a shape of a disc, a shaft 54a of a motor 54 being fixed to a center of the disc.

Figure 13:
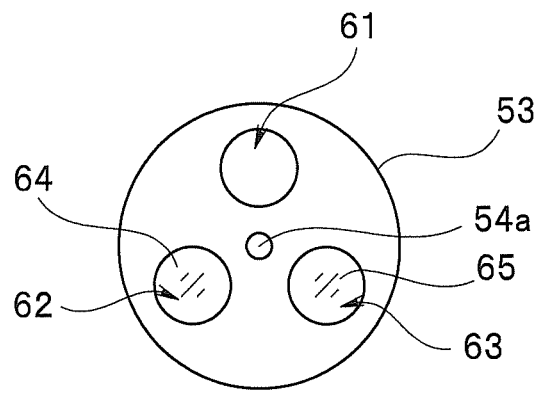
FIG. 13 is a diagram illustrating a configuration of a filter 53 according to the fourth embodiment of the present invention.

FIG. 13 is a diagram illustrating a configuration of the filter 53. In the disc-shaped filter 53, three opening portions 61, 62, 63 are formed in the disc at equal intervals in a circumferential direction, and a bimodal filter 64 is attached to one opening portion 62 from among the opening portions 61, 62, 63, and a trimodal filter 65 is attached to another opening portion 63 from among the opening portions 61, 62, 63. No filter is attached to the opening portion 61.

The bimodal filter 64 is a filter configured to transmit only two types of narrow band light, that is, narrow band light NBL1 having a center wavelength of 410 nm and narrow band light NBL3 having a center wavelength of 540 nm, and prevents transmission of light of other bands.

The trimodal filter 65 is a filter configured to transmit only three types of narrow band light, that is, narrow band light NBL2 having a center wavelength of 460 nm, narrow band light NBL31 having a center wavelength of 515 nm and narrow band light NBL4 having a center wavelength of 630 nm and prevents transmission of light of other bands.

As described above, the light source apparatus 14B includes the lamp 52, which is a light source configured to emit white light, and the filter 65 having at least a trimodal characteristic, the filter 65 being configured to upon receipt of white light, transmit narrow band light NBL31 including a wavelength that is minimally absorbed by blood within light of a green wavelength band, narrow band light NBL2 whose wavelength is shorter and which is more absorbed by blood than the green wavelength band and narrow band light NBL4 whose wavelength is longer and which is less absorbed by blood than the green wavelength band.

A system control circuit 21 transmits information of a set observation mode to a light source control circuit 51, and a light source control circuit 31 drives the motor 54 to turn the filter 53 so that light passed through the lens 55 from the lamp 52 falls on the opening portion corresponding to the observation mode.

In a normal light observation mode, in order to cause light from the lamp 52 to pass through the opening portion 61, the light source control circuit 51 drives the motor 54 to turn the filter 53 so that the opening portion 61 is located on an optical path of light from the lamp 52.

In a narrow band light observation mode, in order to cause light from the lamp 52 to pass through the bimodal filter 64 of the opening portion 62, the light source control circuit 51 drives the motor 54 to turn the filter 53 so that the opening portion 62 is located on the optical path of light from the xenon lamp 52.

In a bleeding point observation mode, in order to cause light from the lamp 52 to pass through the trimodal filter 65 of the opening portion 63, the light source control circuit 51 drives the motor 54 to turn the filter 53 so that the opening portion 63 is located on the optical path of light from the lamp 52.

In other words, the light source control circuit 51 can emit desired illuminating light from the light source apparatus 14B by driving the motor 54 according to an observation mode.

In each observation mode, illuminating light from the light source apparatus 14B is received by the image pickup device 12b including an on-chip color filter.

Therefore, in the normal light observation mode, the image pickup section 12a receives reflected light from a subject irradiated with white light.

In the narrow band light observation mode, the image pickup section 12a receives reflected light from a subject irradiated with two types of narrow band light, that is, narrow band light NBL1 having a center wavelength of 410 nm and narrow band light NBL3 having a center wavelength of 540 nm.

In the bleeding point observation mode, the image pickup section 12a receives reflected light from a subject irradiated with three types of narrow band light, that is, narrow band light NBL2 having a center wavelength of 460 nm, narrow band light NBL31 having a center wavelength of 515 nm and narrow band light NBL4 having a center wavelength of 630 nm.

Therefore, in each observation mode, an illumination method is a simultaneous method.

The video processor 13 generates an image signal of a subject irradiated with narrow band light NBL31, the image signal of the subject including a bleeding point in a region representing blood, an image signal of the subject irradiated with narrow band light NBL2 and an image signal of the subject irradiated with narrow band light NBL4 from an image pickup signal outputted by the image pickup device 12b upon receipt of reflected light from the subject irradiated with the narrow band light NBL2, the narrow band light NBL31 and the narrow band light NBL4, extracts a blood pool region having a blood concentration that is lower than a blood concentration of the bleeding point in the image signal, and raises luminance values of the extracted blood pool region and outputs the three image signals.

Therefore, the present embodiment also enables provision of effects that are similar to the effects of the first embodiment.

Also, although in the above-described embodiment, three types of narrow band light, that is, narrow band light NBL2 having a center wavelength of 460 nm, narrow band light NBL31 having a center wavelength of 515 nm and narrow band light NBL4 having a center wavelength of 630 nm are generated using the trimodal filter 65 provided in the filter 53, which is a rotary filter, a mechanism configured to be capable of moving a trimodal filter to an optical path of light from a light source in a direction orthogonal to the optical path according to the bleeding point observation mode may be used.

Fifth Embodiment

Although in the above-described fourth embodiment, a bimodal filter and a trimodal filter are used for illuminating light of a predetermined wavelength band, a light source apparatus according to the present embodiment uses a rotary filter including a plurality of filters that are neither a bimodal filter nor a trimodal filter.

An endoscope apparatus 1D according to the fifth embodiment has a configuration that is substantially the same as the configuration of the endoscope apparatus 1C according to the fourth embodiment. Therefore, in the below description, components that are the same as the components in the endoscope apparatus 1C according to the fourth embodiment are provided with reference numerals that are the same as the reference numerals of the endoscope apparatus 1C and description of such components will be omitted, and only components in the endoscope apparatus 1D according to the fifth embodiment that are different from the components in the endoscope apparatus 1C according to the fourth embodiment will be described.

Figure 14:
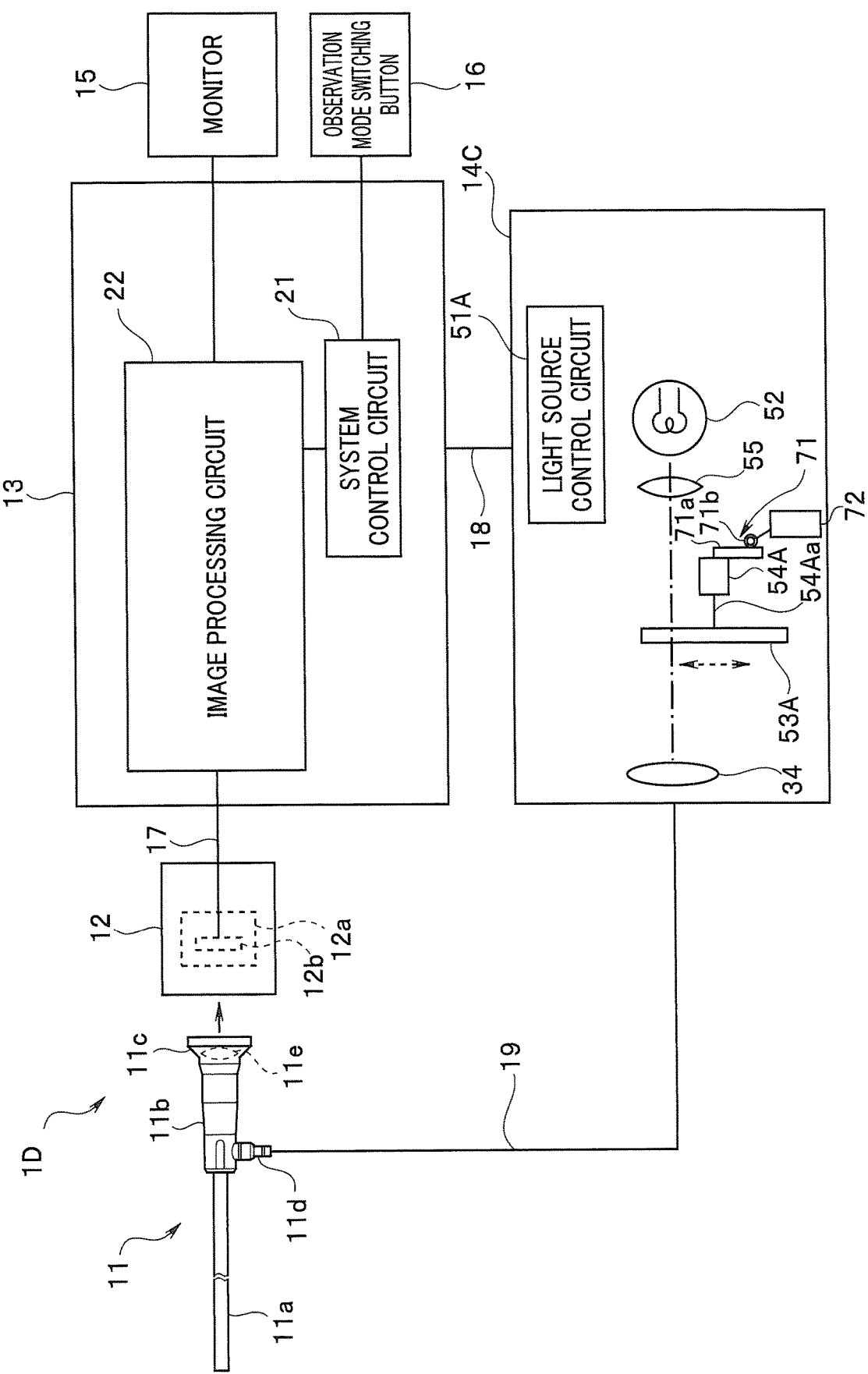
FIG. 14 is a configuration diagram illustrating a configuration of an endoscope apparatus 1D including an image processing apparatus according to a fifth embodiment of the present invention.

FIG. 14 is a configuration diagram illustrating a configuration of an endoscope apparatus 1D including an image processing apparatus according to the fifth embodiment.

A light source apparatus 14C in the endoscope apparatus 1D according to the fifth embodiment includes a collecting lens 34, a light source control circuit 51A, a lamp 52, a rotary filter 53A, a motor 54A configured to rotate the rotary filter 53A, a lens 55, a moving mechanism 71 configured to move the rotary filter 53A in a direction orthogonal to an optical axis of light from the lamp 52, and a motor 72 configured to drive the moving mechanism 71.

The moving mechanism 71 is a rack and pinion mechanism and includes a rack 71a and a pinion 71b. A shaft of the motor 72 is mechanically connected to a rotary shaft of the pinion 71b. The motor 54A is fixed to the rack 71a and moves in the direction orthogonal to the optical axis of light from the lamp 52 as indicated by the dotted arrow, upon driving of the motor 72.

The light source control circuit 51A controls a position, in the direction orthogonal to the optical axis of light from the lamp 52, of the rotary filter 53A according to an observation mode.

The rotary filter 53A has a shape of a disc, and a shaft 54Aa of the motor 54A is fixed to a center of the disc.

Figure 15:
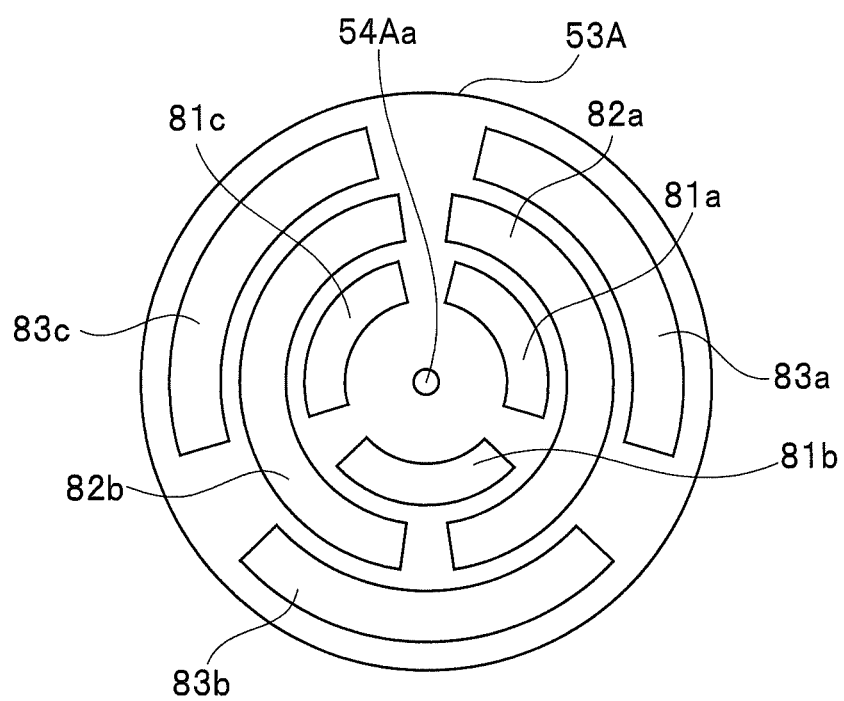
FIG. 15 is a diagram illustrating a configuration of a rotary filter 53A according to the fifth embodiment of the present invention.

FIG. 15 is a diagram illustrating a configuration of the rotary filter 53A.

The rotary filter 53A includes three filter groups provided toward an outer circumference from the center of the disc.

A first filter group on the innermost circumferential side is used in a normal light observation mode and includes three filters 81a, 81b, 81c disposed circumferentially. The filters 81a, 81b and 81c are blue (B), green (G) and red (R) filters, respectively, for outputting frame-sequential light having a spectral characteristic for normal light observation.

A second filter group on the outer circumferential side of the first filter group is used in a narrow band light observation mode and includes two filters 82a, 82b disposed circumferentially. The filters 82a and 82b are filters for narrow band light NBL1 having a center wavelength of 410 nm and narrow band light NBL3 having a center wavelength of 540 nm, respectively, for outputting frame-sequential light having a spectral characteristic for narrow band light observation.

The third filter group on the outer circumferential side of the second filter group is used in a bleeding point observation mode and includes three filters 83a, 83b, 83c disposed circumferentially. The filters 83a, 83b and 83c are filters for narrow band light NBL2 having a center wavelength of 460 nm, narrow band light NBL31 having a center wavelength of 515 nm and narrow band light NBL4 having a center wavelength of 630 nm, respectively, for outputting frame-sequential light having a spectral characteristic for bleeding point observation.

The system control circuit 21 transmits information of a set observation mode to the light source control circuit 51A, and the light source control circuit 51A drives the motor 54 and 72 to control rotation and a position of the filter 53 so that light passed through the lens 55 from the lamp 52 falls on the filter group corresponding to the observation mode and frame-sequential light is outputted.

In the normal light observation mode, the light source control circuit 51A drives the motor 72 to move the rotary filter 53A so that light from the lamp 52 falls on the first filter group, and drives the motor 54 to rotate the rotary filter 53A around the shaft 54Aa to output frame-sequential light having a spectral characteristic for normal light observation toward the collecting lens 34.

In the narrow band light observation mode, the light source control circuit 51A drives the motor 72 to move the rotary filter 53A so that light from the lamp 52 falls on the second filter group and also drives the motor 54 to rotate the rotary filter 53A around the shaft 54Aa to output frame-sequential light having a spectral characteristic for narrow band light observation toward the collecting lens 34.

In the bleeding point observation mode, the light source control circuit 51A drives the motor 72 to move the rotary filter 53A so that light from the lamp 52 falls on the third filter group and also drives the motor 54 to rotate the rotary filter 53A around the shaft 54Aa to output frame-sequential light having a spectral characteristic for bleeding point observation toward the collecting lens 34.

The light source apparatus 14C includes the lamp 52, which is a light source configured to emit white light, and the rotary filter 53A including the filter 83a configured to transmit narrow band light NBL2 whose wavelength is shorter and which is more absorbed by blood than a green wavelength band, the filter 83b configured to transmit narrow band light NBL31 including a wavelength that is minimally absorbed by blood within light of the green wavelength band and the filter 83c configured to transmit narrow band light NBL4 whose wavelength is longer and which is less absorbed by blood than the green wavelength band, and upon the rotary filter 53A being rotated, emits narrow the band light NBL2, the narrow band light NBL31 and the narrow band light NBL4 in a predetermined order.

In other words, the light source control circuit 51 can cause desired illuminating light to be emitted in a predetermined order from the light source apparatus 14C by driving the motors 54 and 72 according to an observation mode.

In each observation mode, illuminating light from the light source apparatus 14C is received by a monochrome image pickup device 12b.

Therefore, in the normal light observation mode, an image pickup section 12a receives reflected light from a subject irradiated with frame-sequential light having a spectral characteristic for normal light observation.

In the narrow band light observation mode, the image pickup section 12a receives reflected light from a subject irradiated frame-sequentially with two types of narrow band light, that is, narrow band light NBL1 having a center wavelength of 410 nm and narrow band light NBL3 having a center wavelength of 540 nm.

In the bleeding point observation mode, the image pickup section 12a receives reflected light from a subject irradiated frame-sequentially with three types of narrow band light, that is, narrow band light NBL2 having a center wavelength of 460 nm, narrow band light NBL31 having a center wavelength of 515 nm and narrow band light NBL4 having a center wavelength of 630 nm.

The video processor 13 generates an image signal of a subject irradiated with the narrow band light NBL31, the image signal of the subject including a bleeding point in a region representing blood, an image signal of the subject irradiated with the narrow band light NBL2 and an image signal of the subject irradiated with the narrow band light NBL4 from an image pickup signal outputted by the image pickup device 12b upon receipt of reflected light from the subject irradiated with the narrow band light NBL2, the narrow band light NBL31 and the narrow band light NBL4, extracts a blood pool region having a blood concentration that is lower than a blood concentration of the bleeding point in the image signal for the narrow band light NBL31, and raises luminance values of the extracted blood pool region and outputs the three image signals.

Therefore, in each observation mode, an illumination method is a frame-sequential method.

Therefore, the present embodiment also enables provision of effects that are similar to the effects of the first embodiment.

Sixth Embodiment

Although each of the above first to fifth embodiments, a subject is irradiated with narrow band light having a center wavelength of 515 nm, it is possible that: a subject is irradiated with light other than the narrow band light having a center wavelength of 515 nm; an image of the narrow band light having a center wavelength of 515 nm is obtained by means of spectral estimation processing; and the processing in the first to fifth embodiments is performed using the obtained spectral estimation image.

In other words, all or part of the first to third images may be obtained by means of spectral estimation.

In a bleeding point observation mode, one image signal may be obtained by forming an image of a subject irradiated with narrow band light NBL2 whose wavelength is shorter and which is more absorbed than a green wavelength band. Another image signal may be obtained by forming an image of the subject irradiated with narrow band light NBL31 including a wavelength that is minimally absorbed by blood within the green wavelength band, the image of the subject including a bleeding point. Still another image signal may be obtained by forming an image of the subject irradiated with narrow band light NBL4 whose wavelength is longer and which is less absorbed by blood than the green wavelength band.

The same applies to respective image signals in each of a narrow band light observation mode and a normal light observation mode.

Even if spectral estimation images are used, effects that are similar to the effects of the first embodiment can be obtained.

Here, although the endoscope in the endoscope apparatus according to each of the above-described embodiments is a rigid endoscope, the endoscope connected to the video processor may be a flexible endoscope including a flexible insertion portion.

Still furthermore, in the video processor 13 in the endoscope apparatus according to each of the above-described embodiments, various types of image processing such as image generation are performed by the image processing circuit 22 but may be performed by software. In such a case, a video processor 13, which is an image processing apparatus, includes a processor for image processing, the processor including hardware such as a CPU, a ROM and a RAM. Software programs for various types of processing are stored in the ROM, and the video processor 13 can perform various types of image processing upon the software programs being read and developed in the RAM and executed by the CPU of the processor.

As described above, the above-described respective embodiments and the respective modifications each enable provision of an image processing apparatus capable of providing display on a monitor in such a manner that a site causing bleeding, that is, a bleeding point can clearly be viewed when a mucous surface is covered by blood, using a wavelength band other than a range of from 585 nm to 615 nm.

The present invention is not limited to the above-described embodiments and various changes, alterations and the like are possible without departing from the spirit of the present invention.

What is claimed is:

1. An image processing apparatus comprising:
a region extracting circuit configured to receive an input of a first image signal obtained as a result of forming an image of a subject irradiated with first narrow band light including a wavelength within a range of from 505 nm to 515 nm as a center wavelength in a green wavelength band, the wavelength being minimally absorbed by blood, and extract, of a bleeding point and a blood pool region having a blood concentration that is lower than a blood concentration of the bleeding point in the image of the subject, the blood pool region from the first image signal; and
an image generating circuit configured to subject the blood pool region extracted by the region extracting circuit in the image of the subject generated using the first image signal to processing for displaying the blood pool region in a color that is different from a color of the bleeding point, wherein
the image generating circuit raises a luminance value of the blood pool region in either the first image signal or a second image signal obtained as a result of forming an image of the subject irradiated with second narrow band light that is blue narrow band light whose wavelength is shorter than the first narrow band light, the second narrow band light being more absorbed by the blood than the first narrow band light.

2. The image processing apparatus according to claim 1, wherein the image generating circuit raises the luminance value of the blood pool region by replacing the luminance value of the blood pool region in the first image signal with a luminance value of the blood pool region in a third image signal obtained as a result of forming an image of the subject irradiated with third narrow band light that is red narrow band light whose wavelength is longer than the first narrow band light, the third narrow band light being less absorbed by the blood than the first narrow band light.

3. The image processing apparatus according to claim 1, wherein the image generating circuit further generates image signals in which the first image signal, the second image signal and a third image signal obtained as a result of forming an image of the subject irradiated with third narrow band light that is red narrow band light whose wavelength is longer than the first narrow band light, the third narrow band light being less absorbed by the blood than the first narrow band light, are allocated to respective different colors.

4. The image processing apparatus according to claim 2, wherein the image generating circuit further generates image signals in which the first image signal, the second image signal and the third image signal are allocated to respective different colors.

5. An image processing apparatus comprising:
a region extracting circuit configured to receive an input of a first image signal obtained as a result of forming an image of a subject irradiated with first narrow band light including a wavelength within a range of from 505 nm to 515 nm as a center wavelength in a green wavelength band, the wavelength being minimally absorbed by blood, and extract, of a bleeding point and a blood pool region having a blood concentration that is lower than a blood concentration of the bleeding point in the image of the subject, the blood pool region from the first image signal; and an image generating circuit configured to subject the blood pool region extracted by the region extracting circuit in the image of the subject generated using the first image signal to processing for displaying the blood pool region in a color that is different from a color of the bleeding point, wherein the region extracting circuit receives an input of an image signal including a plurality of pixels as the first image signal, receives an input of an image signal including a plurality of pixels as a second image signal obtained as a result of forming an image of the subject irradiated with second narrow band light that is blue narrow band light whose wavelength is shorter than the first narrow band light, the second narrow band light being more absorbed by the blood than the first narrow band light, calculates degrees of difference between the respective pixels in the first image signal and the respective corresponding pixels in the second image signal on a pixel-by-pixel basis, and extracts a region of a pixel where the degree of difference for the pixel exceeds a threshold value for extracting the blood pool region of the bleeding point and the blood pool region in the image of the subject, as the blood pool region.

6. The image processing apparatus according to claim 5, wherein the degrees of difference are represented by differences between the respective pixels in the first image signal and the respective corresponding pixels in the second image signal.

7. An image processing apparatus comprising a processor including hardware, wherein:

the processor receives an input of a first image signal obtained as a result of forming an image of a subject irradiated with first narrow band light including a wavelength within a range of from 505 nm to 515 nm as a center wavelength in a green wavelength band, the wavelength being minimally absorbed by blood, and extracts, of a bleeding point and a blood pool region having a blood concentration that is lower than a blood concentration of the bleeding point in the image of the subject, the blood pool region from the first image signal; and the processor subjects the extracted blood pool region in the image of the subject generated using the first image signal to processing to raise a luminance value of the blood pool region in either the first image signal or a second image signal obtained as a result of forming an image of the subject irradiated with second narrow band light that is blue narrow band light whose wavelength is shorter than the first narrow band light, the second narrow band light being more absorbed by the blood than the first narrow band light, for displaying the blood pool region in a color that is different from a color of the bleeding point.

* * * * *